United States Patent
Elsner et al.

(10) Patent No.: US 6,640,124 B2
(45) Date of Patent: Oct. 28, 2003

(54) IMAGING APPARATUS AND METHODS FOR NEAR SIMULTANEOUS OBSERVATION OF DIRECTLY SCATTERED LIGHT AND MULTIPLY SCATTERED LIGHT

(75) Inventors: Ann E. Elsner, Reading, MA (US); Stephen A. Burns, Reading, MA (US); Andreas W. Dreher, Escondido, CA (US); Robert H. Webb, Lincoln, MA (US)

(73) Assignee: The Schepens Eye Research Institute, Boston, MA (US)

( * ) Notice: Subject to any disclaimer, the term of this patent is extended or adjusted under 35 U.S.C. 154(b) by 17 days.

(21) Appl. No.: 09/919,498

(22) Filed: Jul. 31, 2001

(65) Prior Publication Data

US 2002/0101566 A1 Aug. 1, 2002

Related U.S. Application Data

(63) Continuation-in-part of application No. 09/846,029, filed on Apr. 30, 2001, now abandoned, which is a continuation-in-part of application No. 09/016,112, filed on Jan. 30, 1998, now Pat. No. 6,236,877.

(51) Int. Cl.[7] .................................................. A61B 5/05
(52) U.S. Cl. ....................... 600/407; 600/473; 600/476; 356/342; 351/221
(58) Field of Search ................................. 600/407, 473, 600/475, 476, 310; 356/337, 342; 351/221

(56) References Cited

U.S. PATENT DOCUMENTS

| | | | |
|---|---|---|---|
| 3,658,405 A | 4/1972 | Pluta | 350/12 |
| 4,213,678 A | 7/1980 | Pomerantzeff et al. | 351/7 |
| 4,555,179 A | 11/1985 | Langerholc et al. | 356/342 |
| 4,764,005 A | 8/1988 | Webb et al. | 351/205 |
| 4,838,679 A | 6/1989 | Bille | 351/205 |
| 4,844,617 A | 7/1989 | Kelderman et al. | 356/372 |
| 5,028,802 A | 7/1991 | Webb et al. | 250/571 |
| 5,137,355 A | 8/1992 | Barbour et al. | 356/342 |
| 5,303,709 A | 4/1994 | Dreher et al. | 128/665 |
| 5,760,901 A | 6/1998 | Hill | 356/345 |
| 5,770,454 A | 6/1998 | Essenpreis et al. | 436/164 |
| 5,787,890 A | 8/1998 | Reiter et al. | 128/665 |
| 5,813,987 A | 9/1998 | Modell et al. | 600/473 |
| 5,830,147 A | 11/1998 | Feke et al. | 600/479 |
| 5,886,768 A | 3/1999 | Knopp et al. | 351/212 |
| 5,963,300 A | 10/1999 | Horwitz | 351/209 |
| 5,973,779 A | 10/1999 | Ansari et al. | 356/301 |
| 6,002,480 A | 12/1999 | Izatt et al. | 356/345 |
| 6,003,993 A | 12/1999 | Webb | 351/221 |
| 6,016,367 A | 1/2000 | Benedetti et al. | 382/275 |
| 6,112,114 A | 8/2000 | Dreher | 600/476 |
| 6,236,877 B1 | 5/2001 | Elsner et al. | 600/407 |

FOREIGN PATENT DOCUMENTS

WO  WO 02/088818 A1  11/2002

OTHER PUBLICATIONS

M.B.Mellem Kairala et al., "Polarimetric Analysis of the Peripapillary Hyperpigmentation in Glaucoma Patients", ARVO Abstract #245, 2002.

Elsner et al.; "Multiply Scattered Light Tomography and Confocal Imaging: Detecting Neovascularization in Age-Related Macular Degeneration" Optics Express, 7(2): 95–106, (Jul. 17, 2000).

(List continued on next page.)

Primary Examiner—Marvin M. Lateef
Assistant Examiner—Barry Pass
(74) Attorney, Agent, or Firm—Foley Hoag LLP

(57) ABSTRACT

An apparatus and a method are disclosed for separating light remitted by a target into a directly scattered light component and at least one multiply scattered light component, detecting the components at least substantially simultaneously, and forming independent sets of image information from each component. The apparatus and the method can be employed in conjunction with techniques such as scanning and tomography to attain precise imaging of biological tissue, including the retina of the eye.

61 Claims, 13 Drawing Sheets

OTHER PUBLICATIONS

Form PCT/ISA/210, International Search Report for PCT/US/02/24254 Mar. 20, 2003), Applicant: The Schepens Bye Research Institute.

Chen et al.; "Clinical Vision Sciences 7", 521–530, 1992.

Elsner et al.; "Infrared Imaging of Sub–retinal Structures in the Human Ocular Fundus", Vision Research 36(1): 191–205, (1996).

Elsner et al.; "Foveal Cone Photopigment Distribution: Small Alterations Associated with Macular Pigment Distribution", Investigative Ophthalmology & Visual Science, 39(12), (1998).

Kunze et al.; "Spatial Extent of Pigment Epithelial Detachments in Age–Related Macular Degeneration", Ophthalmology 106(9): 1830–1840, (Sep. 1999).

Beausencourt et al.; "Infrared Scanning Laser Tomolography of Macular Cysts", Ophthalmology, 107(2):375–385, (Feb. 2000).

Beausencourt et al.; "Quantitative Analysis of Macular Holes With Scanning Laser Tomography", Ophthalmology 104 (12):2018–2029, (Dec. 1997).

Zambarakji et al.; "Volumetric Analysis of Early Macular Edema With the Heidelberg Retina Tomograph in Diabetic Retinopathy", Ophthalmology 105(6): 1051–1059, (Jun. 1998).

Rigaudiere et al.; "Value of Scanning Laser Ophthalmoscopy In the Evaluation of the Visual Function of the Visual Function of 47 Patients With Moderate Cataracts Associated with Maculopathy—II. Value of Focal Visual Evoked Cortical Potentials In Macular Functional Evaluation", Clin. Vision Sci. 7(6): 541–549, (1992).

Elsner et al.; "Scanning Laser Reflectometry of Retinal and Subretinal Tissues", Vision Science and Its Applications, TOPS Vol. 35, Series Editor: Tingye Li, pp.272–278, (Jun. 2000).

Elsner et al.; "Multiply Scattered Light Tomography and Confocal Imaging: Detecting Neovascularization in Age–Related Macular Degeneration", Vision Science and its Applications (OSA Trends in Optics and Photonics Series), vol. 35, pp. 279–285.

Elsner et al.; "Separating Sub–retinal and Retinal Structures Using Polarimetric Imaging", Investigative Ophthalmology and Visual Science, Abract. p. S706, No. 3808–B950, ARVO Annual Meeting, 2001.

Elsner et al.; "New Devices for Retinal Imaging and Functional Evaluation", Practical Atlas of Retinal Disease and Therapy, Second Edition edited by W. R. Freeman, Lippincott Publishers, Philadelphia, Chap. 2, pp. 19–55, (1997).

Dreher et al.; "Active Optial Depth Resolution Improvement of the Laser Tomographic Scanner", Applied Optics, 28(4): 804–808, (Feb. 15, 1989).

Meyer et al.; "Blind Spot Size Depends on the Optic Disc Topography: A Study Using SLO Controlled Scotometry and the Heidelberg Retina Tomograph", British Journal of Ophthalmology 81:355–359, (1997).

Bartsch et al.; "Confocal Laser Tomographic Analysis of the Retina in Eyes with Macular Hole Formation and Other Focal Macular Diseases", American Journal of Ophthalmology 108:277–287, (Sep. 1989).

Elsner et al.; "Multiply Scattered Light Tomography", Lasers and Light 8(3): 193–202 (1998).

Remky et al., "Infrared Imaging of Cystoid Macular Edema", Graefe's Arch. Clin. Exp. Ophthalmology, 237: 897–901, (1999).

Elsner et al.; "Scanning Laser Reflectometry of Retinal and Subretinal Tissues", Optics Express 6 (13): 243–250 (Jun. 19, 2000).

Elsner et al.; "Multiply Scattered Light Tomography and Confocal Imaging: Detecting Neovascularization in Age–Related Macular Degeneration" Optics Express, 7(2): 95–106, (Jul. 17, 2000).

Dreher et al.; "Reproducibility of Topographic Measurements of the Normal and Glaucomatous Optic Nerve Head with the Laser Tomographic Scanner", American Journal Of Ophthalmology, 111:221–229, (Feb. 1991).

Weinberger et al.; "Three–dimentional Measurements of Idiopathic macular Holes Using a Scanning Laser Tomograph", Ophthalmology 102(10):1445–1449, (Oct. 1995).

Elsner et al.; "Scattered Light Tomography:Instrumentation and Ocular Fundus Data with a Verical Cavity surface Emitting Laser", Vision Science and its Applications, vol. 1: SaB1-1—SaB1-4, (Jan. 31–Feb. 3, 1997).

Elsner et al.; "Detecting AMD with Multiply Scattered Light Tomography"; International Ophthalmology 23: 245–250, 2001.

Hartnett et al.; "Characteristics of Exudative Age–related Macular Degeneration Determined In Vivo with Confocal and Indirect Infrared Imaging" Ophthalmology 103(1):58–71, (Jan. 1996).

Form PCT/ISA/210, International Search Report for PCT/US/01/13741 (Apr. 30, 2001), Applicant: The Schepens Eye Research Institute.

IMAGING APPARATUS AND METHODS FOR NEAR SIMULTANEOUS OBSERVATION OF DIRECTLY SCATTERED LIGHT AND MULTIPLY SCATTERED LIGHT

This application is a continuation-in-part of U.S. patent application Ser. No. 09/846,029, filed Apr. 30, 2001, abandoned which is a continuation-in-part of U.S. patent application Ser. No. 09/016,112, filed Jan. 30, 1998, now U.S. Pat. No. 6,236,877. The contents of the above-referenced documents are hereby incorporated in their entirety.

FIELD OF THE INVENTION

This invention relates to the field of image processing. More particularly, it relates to methods and devices for separating multiply scattered light from directly scattered light. The invention further relates to methods and devices that utilize the resultant data sets in the characterization of an optical target beyond that routinely performed in directly scattered light.

BACKGROUND OF THE INVENTION

In many imaging applications, the object to be imaged includes a highly remittive layer. When light illuminates such an object, the resulting image consists of a directly scattered light component reflected from this highly remittive layer and a multiply scattered light component that is scattered from points that are within the object but outside the highly remittive layer. Because the layer is highly remittive, the directly scattered light component tends to dominate the image. As a result, it is difficult to capture the multiply scattered light component of the image.

An example of an object having a highly remittive layer is the human retina. In the retina, certain structures are visible only by examination of the directly scattered light component of the image. These structures cannot be seen clearly by examination of the multiply scattered light component. Examples of such structures include small blood vessels and superficial features of the optic nerve head. Conversely, there exist other retinal structures, such as drusen, clumped pigment, choroidal tumors, subretinal new blood vessels, subretinal edema, and the choroidal rim of the optic nerve head, which are visible to a far greater extent in the multiply scattered light component than in the directly scattered light component.

In some applications, such as ophthalmologic ones, it is desirable to locate precisely a structure which can be imaged in the multiply scattered light component with respect to a known feature observable only in the directly scattered light component. For example, it may be useful to know that a particular region of drusen or edema is located near the intersection of two blood vessels. Conversely, it is desirable in some applications to locate precisely a structure that can be imaged in the directly scattered light component with respect to a known feature observable only in the multiply scattered light component. For example, it may be desirable to use the choroidal rim, a feature readily observed in the multiply scattered light component, as a point of reference for imaging blood vessels in the vicinity of the macula.

A known technique for separating a multiply scattered light component from a directly scattered light component is to illuminate the retina with a point light source and to direct the remitted image field through a field stop confocal to the light source. By providing the field stop with a pinhole aperture, one can observe the directly scattered light component of the image. Alternatively, by providing a field stop with an annular opening, one can observe the multiply scattered light component of the image. These techniques are described in Elsner A. E., Burns S. A., Weiter J. J., and Delori F. C., *Infrared imaging of subretinal structures in the human ocular fundus,* Vision Research 36, 191–205, 1996.

Using the foregoing technique, one can provide a field stop with a pinhole aperture, observe the directly scattered light component of the image, replace the pinhole aperture with an annular aperture, and then observe the multiply scattered light component of the image. By scanning in two dimensions, one can generate a two-dimensional image that includes only the multiply scattered light component and create another image that includes only the directly scattered light component. Similarly, by using known techniques of tomography, one can obtain pairs of cross-sections, each pair including one image based on the multiply scattered light component and another based on the directly scattered light component.

A disadvantage of the foregoing technique is that a significant time interval elapses between the measurement of the directly scattered light component and the subsequent measurement of the multiply scattered light component. This interval arises because of the time required to replace the pinhole aperture with an annular aperture. A lengthy interval leads to artifacts in comparison or other combination of information from the two components. Such artifacts reduce the effectiveness of image or data processing techniques in yielding meaningful information concerning the light scattering properties of the target. A lengthy interval allows potential motion or other alterations concerning the target to preclude accuracy in such observations, comparisons, or computations.

Using the forgoing technique, one can, in principle, precisely locate a structure visible in one component relative to a feature visible in the other component by capturing an image or collecting data restricted primarily to the directly scattered field and overlay it on the image or data of the multiply scattered field. By aligning the image or data from the multiply scattered light component with the image or data from the directly scattered light component, one can endeavor to locate a structure visible only in one component relative to a structure visible only in the other component.

In practice, however, the effectiveness of localization is also severely limited by the time interval that elapses between collecting the data from the directly scattered light component and the multiply scattered light component. This is because a target can undergo motion or change over time. For example, the retina is subject to rapid and unpredictable motion. As a result, in the interval, referred to as a blanking interval, that elapses as the two apertures are alternated, the retina may have moved by some unknown amount or in some unknown direction. Typically the mechanical inertia associated with alternating between two apertures prevents the blanking interval from being made short enough to capture two successive images without significant alteration to the target, e.g. movement of the retina, between images. Since a patient cannot entirely control eye movements, the position of the retina during observation of the multiply scattered light component will, in general, not be the same as the position of the retina during observation of the directly scattered light component. This unpredictable motion or alteration of the target, e.g. the retina, causes unpredictable errors in the reliable alignment of two or more image components or data sets and the further processing of the data therein.

SUMMARY OF THE INVENTION

What is desirable in the art is an apparatus and method for reducing the blanking interval, thereby permitting observation of the directly scattered light component and the multiply scattered light component of a target at least substantially simultaneously. For example, if the blanking interval could be made short enough, the retinal target would move or be altered by a negligible amount between the observation of the directly scattered light component and the observation of the multiply scattered light component.

This invention provides apparatus and methods permitting an operator to switch easily between observation of the directly scattered light component and observation of the multiply scattered light component of the image. Near simultaneous collection of the separated components allows their use in further observation, comparison, or computations for characterizing an object, specimen, or structure. In certain embodiments, the invention provides apparatus and methods for observation, evaluation, diagnosis, and therapeutic manipulation of anatomical regions of interest. In certain embodiments, the invention provides apparatus and methods for observation, evaluation, diagnosis, and therapeutic manipulation of the human retina. In the ophthalmologic field, it is desirable to provide an imaging apparatus to allow an operator to use substantially simultaneously both the directly scattered light component and the multiply scattered light component of an image of the human ocular fundus to test adequately for potential pathology.

In certain embodiments, the invention provides apparatus and methods for detecting features in one light component to be used as points of reference for locating distinct features in the other light component. In certain embodiments, the invention provides apparatus and methods for aligning the apparatus according to localization information derived from at least one light component.

It is useful to make computations depending on aspects of both components, using information from each either in succession, simultaneously, or in an iterative manner. Such images, imaging data, computation, or simultaneous or successive comparisons are then readily collected and transmittable in a form so as to be useful in the diagnosis and treatment of eye disease.

In certain applications, such as ophthalmologic ones, it is desirable to locate precisely a structure that can be imaged in the multiply scattered light component with respect to a known feature observable only in the directly scattered light component or vice versa. For example, in the eye it may be useful to know that a particular region of drusen, clumped pigment, choroidal tumors, subretinal new blood vessels, subretinal edema, or the choroidal rim of the optic nerve head, each of which is visible in the multiply scattered light component, is located near the intersection of two blood vessels or superficial cysts that are visible in the directly scattered light component from the more superficial layers of the retina.

This invention provides apparatus and methods that permit immediate generation and observation of an entire image derived primarily from multiply scattered light at least substantially simultaneously with an image derived primarily from directly scattered light. The at least substantially simultaneous generation and observation of images from each type of scattered light, in accordance with the invention, facilitates localization of features primarily visible in one component relative to features visible in the other component by reducing to zero duration or nearly eliminating the blanking interval between observations. The blanking interval is reduced such that the target position and orientation do not change substantially between observations. Therefore, localization data determined from the image generated from one light component may be applied readily to the image generated from the other light component, since structures in the target do not move appreciably during the blanking interval.

The structures more visible in multiply scattered light, such as the choroidal rim of the optic nerve head or subretinal new vessel membranes, may be used to locate a specific portion of the retina for further diagnosis or treatment. Localization can be further improved in some cases by combining the information from directly scattered light and multiply scattered light, but this depends upon reliably accurate registration of the information. The multiply scattered light components as disclosed by Elsner et al. (1996) have been difficult to utilize or interpret.

For the purposes of the present invention, the word "remit" refers to any instance of optical radiation resulting from an incident illumination, including by way of example transmission, reflection, scattering, and fluorescence; "remitter" refers to any object that radiates incident electromagnetic radiation in any way, including by way of example transmission, reflection, scatter, or fluorescence; and "remittance" refers to all manner of optical radiation from a target, including by way of example, electromagnetic radiation that is transmitted, reflected, scattered, or fluoresced.

The invention provides, in part, an imaging device having an illumination system, a separation device, and a detection system. In operation, the illumination system directs light to a target, thereby generating remitted light including one or more multiply scattered light components and a directly scattered light component. The remitted light is received by a separation device, which substantially separates the multiply scattered light from the directly scattered light, preferably without requiring a physical change in the configuration, position, or geometry of the separation device. The multiply scattered light may be further separated according to the degree and direction of the multiple scattering, as described in Elsner et al, 1996. The separation device directs the substantially separated light to a detection system, whereby the multiply scattered light and the directly scattered light can be detected separately and substantially simultaneously. The detection system can then generate two or more images or data sets, one based on the directly scattered light component, and the other based on the one or more multiply scattered light components.

The detection system in certain practices of the invention may generate two or more images or data sets based on the degree of scatter and the direction of remission. This provides the advantage of probing optically observable properties of a target, such as retinal tissue, in a manner not limited to light that is remitted along a narrow path from the strongest or closest remitters. The polarization state of light may be used to separate the directly scattered light components from the multiply scattered light components, in that light that has been remitted multiple times on most targets is randomly polarized, even if it started out uniformly polarized.

The separation of light into directly scattered and multiply scattered components, in accordance with the invention, facilitates the probing, identification, and classification of various target structures, examples of which include structures in a highly scattering medium, structures that do not provide a strong index of refraction change within a limited volume of tissue, structures that have surfaces that are not orthogonal to the optical axis of the instrument, structures having boundaries that are not orthogonal to the optical axis of the instrument, structures that lie beneath highly remittive structures, structures that differ in polarization properties, structures with varying amounts of index of refraction change per unit volume, or structures having index of refraction changes insufficient or over too great a volume to provide a strong source of interference for coherence imaging.

Examples of targets in the ophthalmologic field include:

edema, which can provide a graded index of refraction change and contain a variety of compounds not found in that configuration in the healthy eye;

a choroidal new vessel membrane or pigment epithelial detachment, which can have a dome-shaped configuration;

cysts or multi-component new vessel complexes having adjacent or overlapping membranes with borders that are mainly parallel to the axis of the instrument;

drusen, the deeper portion of choroidal new vessels, or the choroidal rim of the optic nerve head, which all lie beneath the highly remittive retina;

macular edema, which may contain proteins, lipids, or other compounds as well as fluid that thickens and elevates the retina;

the birefringent cornea, or the retinal ganglion cell axons found in highly polarized nerve fiber bundles, which themselves are understood to have a strong axis of polarization;

choroidal melanoma, which is characterized by nonuniform pigment and blood vessel distribution, and which may therefore absorb varying degrees of light compared to adjacent healthy or abnormal ocular issue; and edematous structures, particularly beneath the retina, which typically do not provide a strong index of refraction change within a small interior volume, particularly when a remittance passes through the scattering overlying structures.

Several classes of embodiments are described. One example includes two remitted light components. These components include, but are not limited to, a directly backscattered light component remitted from an object illuminated on the optical axis of the imaging device and detected on axis and in alignment with an aperture; and a multiply scattered light component that cannot in entirety pass through an aperture that is on the optical axis when the object is illuminated on axis.

A second example provides two or more multiply scattered light components to generate a scattering function. In an embodiment, the edematous structures in and beneath the retina may be probed with such techniques. This example includes, but is not limited to, a first light component that is scattered in a different direction from, or from a smaller focal volume than, the light in a second light component. This permits calculation of a scattering function to characterize the target and structures within it. In an embodiment, such characterization allows the probing of index of refraction changes to detect and quantify properties of structures that do not necessarily have a sharp index of refraction change.

In a third example, the state of polarization of the remitted light is the separation parameter to obtain the directly scattered light component and the multiply scattered light components. One application of such an embodiment is the detection of drusen and other pathological features that remit light in a manner that loses uniform polarization. Light having an initial polarization tends to lose this polarization progressively as it is repeatedly scattered. Light that loses its initial polarization in this way is said to be "randomly polarized" or "depolarized." For light remitted from drusen and other pathological structures, the loss of polarization occurs because such features lie beneath the retinal nerve fiber layer. Light remitted from these features is scattered and depolarized to a greater extent than is light remitted from the retinal nerve fiber layer, a highly remittive layer that retains polarization to a much greater degree. This example includes, but is not limited to, a first component containing light that retains a greater degree of its initial polarization due to being scattered a relatively fewer number of times prior to reaching the detector, and a second component containing light that retains a lesser degree of polarization due to being scattered a relatively greater number of times. An embodiment according to this example permits a more detailed analysis and improvement of the images or data from the directly scattered light component by quantifying both the polarization state and the position of the remitted light, while the multiply scattered light is derived from those light components that are randomly polarized with respect to the illumination on the target. The remitted light may be analyzed by separating it into two orthogonal polarization states that are detected simultaneously or near simultaneously, or into a series of states that are detected in an exactly or nearly simultaneous manner.

Polarization analysis, termed "polarimetry," is widely practiced in the art. Most general polarimeters use the Stokes formalism, and can be made to detect scattered light. Multiply scattered or depolarized light is typically discarded as contaminating radiation. However, as disclosed herein, the analysis of images derived from such light, in accord with practice of this invention, is a particularly powerful method for observation.

In one aspect of the invention, an illumination source directs light onto a target point. Light remitted from this illuminated target point includes a directly scattered light component and at least one multiply scattered light component. A field stop separates the remitted light into these two constituent components and directs the two components to one or more detectors. The field stop is adapted to permit detection of the directly scattered light component and the at least one multiply scattered light component without a physical change in the configuration, placement, or geometry of the field stop, e.g., by using reflective, transmissive, or polarization properties, thereby permitting the two components to be detected at least substantially simultaneously. Moreover, this invention can be practices with exactly simultaneous detection.

The source may be, but is not limited to, a laser, a light emitting diode, a single vertical cavity surface emitting laser (VCSEL) element, an array of VCSEL elements, or a well-focused arc lamp, or any source of light that may be focused sufficiently to serve as a point source and be separated by a system of confocal apertures, or be sufficiently uniformly polarized to undergo separation using polarization state analyzers. A source with relatively low absorption in some wavelengths, such as near infrared wavelengths, compared to other wavelengths, allows for multiply scattered light to be detected. In targets such as the human retina, there is relatively low absorption in the near infrared portion of the spectrum compared with visible wavelength light.

In one embodiment of the invention, the field stop for separating the components of the image includes a first region optically conjugate to the illuminated point and a second region adjacent to the first region. The first region of the field stop can be adapted to receive primarily directly scattered light. The second region of the field stop can be adapted to receive primarily multiply scattered light. Similarly, the first region can be adapted to receive light that is scattered a relatively few number of times, or over a relatively narrow focal volume, while the second region can be adapted to receive light that is scattered a relatively greater number of times or over a relatively broader focal volume. Further, the first region can be adapted to receive light remitted primarily from one direction, while the second region can be adapted to receive light remitted primarily from another direction, so that further comparisons may be made to characterize the target according to its scattering characteristics. This differs from the common method of producing stereo image pairs, one difference being that the computations are not limited to computations of relative geometric distances.

In another example, the first region can be adapted to receive light in one polarization state, and the second region can be adapted to receive light in another polarization state for the purpose of exactly or nearly simultaneous collection of light having varying degrees of multiple scatter. As successive, multiple scattering of light decreases the uniformity of the axes of polarization regardless of the axes of initial polarization, separating polarized light from depolarized light results in separation of the directly scattered light from the at least one multiply scattered light component. Separation of multiply scattered light from directly scattered light on the basis of polarization state may employ comparison of the extent of polarization without regard to the axes of polarization. Optical properties of targets may be characterized by polarization axes of remitted light.

In a further practice of the invention, the field stop may include more than two such regions, for the purpose of separating the remitted light into more than two components. This feature can enable analysis of two or more multiply scattered light components distinguished by the angles or distances at which they are remitted from the target or by other criteria apparent to one of skill in the art. Analysis of multiply scattered light components separated according to this feature of the invention facilitates superior characterization of the sample than is possible by consideration of directly scattered light alone, as is commonly practiced in confocal microscopy. In one example, a structure that has a stronger index of refraction change within a given volume of target will produce components that are scattered fewer times than one that has a weaker index of refraction change, for example due to fluid infiltration associated with edema. Other factors being equal, the less edematous tissue will scatter the light over a smaller volume than will the more edematous tissue. In another example, the structures contained within a volume of the target that are large or of uniform construction and oriented in a relatively perpendicular axis to that of illumination will direct their remittance back in the direction of the illumination, or remit it in a forward direction. Such a structure is the nerve fiber layer and the vitreous interface where it is perpendicular to the target. The structures that are small and relatively randomly oriented will scatter little of the light directly back toward the source of illumination and remit in a broad angle. Such structures are the compounds found within the fluid in a pigment epithelial detachment. In a third example, the detection and localization of the structures that cause multiple scattering events may be improved by using two or more multiply scattered light components collected separately so that light tissue interactions that create a shadowing effect that is visualized as the border of a structure may be combined to obtain a larger or better specified border. An example of this is a region of drusen. One benefit is that sources of scatter that lie outside the plane of focus have a potentially more uniform distribution from the different directions sampled than if sampled from only one direction. These sources of scatter may be removed by comparison or subtraction from the multiply scattered light that characterizes the target.

In one practice of the foregoing embodiment, the second region can be a reflective surface and the first region can be a pinhole aperture in the reflective surface. In this embodiment, the directly scattered light can pass through the pinhole aperture and the multiply scattered light component can be reflected by the reflective surface adjacent to the pinhole aperture. A detector in optical communication with the pinhole aperture can detect the directly scattered light component passing through the pinhole aperture. Another detector in optical communication with the reflective surface surrounding the aperture can detect the multiply scattered light component reflected by the reflective surface. Accordingly, the directly scattered light component and the multiply scattered light component can be detected substantially simultaneously by two different detectors.

Similarly, the light passing through a somewhat smaller aperture or one that is somewhat less displaced with respect to the optical axis of illumination can have undergone scattering a relatively fewer number of times, in comparison to light remitted from a relatively smaller focal volume, or remitted light from a predominantly different direction than light passing through a somewhat larger aperture or displaced somewhat more. Accordingly, the two or more components differing in the aforementioned scattering properties can be detected at least substantially simultaneously by two or more different detectors. A scattering function for regions within the target may then be computed from data derived from the two or more components.

Alternately, the first region can be a reflective surface and the second region can be an annular aperture surrounding the reflective surface. Thus, the multiply scattered light can pass through the aperture, and the reflective surface within the annular aperture can reflect the directly scattered light component of the image.

Similarly, the light reflecting from a somewhat smaller area or one that is somewhat less displaced with respect to the optical axis of illumination can have scattered a relatively fewer number of times, in comparison to light remitted from a relatively smaller focal volume, or from a predominantly different direction than light reflecting off a somewhat larger area or displaced somewhat more. Accordingly, the two or more components differing in the aforementioned scattering properties can be detected substantially simultaneously by two or more different detectors.

The separation of directly scattered and multiply scattered light can also be realized by providing a first region that comprises the end of an optical fiber or a portion of an end of an optical fiber bundle having a plurality of fibers. In this realization of the embodiment, the directly scattered light component incident on the end of the optical fiber can be transmitted through the fiber to a detector.

In certain embodiments, the functions of separation and of detection can be consolidated, e.g., by using a bundle of optical fibers. In such embodiments, the first region comprises one or more fibers of the bundle, and the second region comprises other fibers of the bundle. Thus, as described above, fibers of the first region can transmit the directly scattered light component to a first detector, and fibers of the second region can transmit the directly scattered light component to a second detector or detectors, thereby permitting the directly scattered light component and the multiply scattered light components to be detected individually.

A further embodiment of the invention employs time-division multiplexing and a single detector in optical communication with a separation device, which detects both the directly scattered light component and at least one multiply scattered light component of the remitted light. In this embodiment, the illumination source can be capable of alternately emitting light from two or more adjacent locations. The light is emitted toward the target and subsequently remitted toward a separation device. The separation device can have a first region in optical communication with a detector and a second region adjacent to the first region. In operation, light from one location of the illumination source can be directed to a target during a first interval. The target then remits light comprising a directly scattered light component and a multiply scattered light component or components.

The separation device can be configured such that the first region receives primarily directly scattered light when the target is illuminated with light from the first location, and the second region receives primarily the multiply scattered light. Light from the second location of the illumination source can then be directed to the target, whereby the directly scattered light component of the remitted light is directed to the second region of the separation device and the first region receives primarily multiply scattered light, which is directed to the detector. Thus, rapid alternation between light emitted by the at least two locations of the illumination source enables the directly scattered light component and the at least one multiply scattered light component remitted by the target to be detected substantially simultaneously. The rate at which the light switches between illumination source locations is directly related to the rate at which the detection switches between remitted light components.

Similarly, the first light source location can be positioned with respect to the target and first region such that the light reaching the detector during the first interval is scattered a relatively fewer number of times, from a relatively smaller focal volume or from a relatively different direction, than the light reaching the detector during the second interval. Thus, rapid alternation between light emitted from two or more locations of the illumination source permits multiply scattered light components and directly scattered light components remitted by the target to be detected substantially simultaneously. This and other embodiments of the invention can be constructed to enable two or more locations of illumination to be detected during two or more different time intervals. A plurality of locations disposed in a two-dimensional array may be used as an illumination source, as described in Elsner et al, 1998a.

One illustrative embodiment has two light sources, with a first source and a second source adjacent to the first light source, to illuminate adjacent points on the target in alternate intervals. During a first interval, the first source illuminates the target at a first illuminated point optically conjugate to a pinhole aperture in a field stop. Directly scattered light from the first illuminated point can pass through the pinhole in the field stop to the detector, while most of the multiply scattered light remitted by the target is blocked by the field stop.

During a second interval, the converse occurs. The second source illuminates the target at a second illuminated point optically conjugate to a point adjacent to the pinhole aperture. This second illuminated point is not optically conjugate to the pinhole aperture. Consequently, multiply scattered light, which can originate from areas adjacent to or from a volume surrounding the first illuminated point, passes through the pinhole aperture in the field stop to the detector. Meanwhile, the remainder of the field stop blocks the directly scattered light.

In a further embodiment, a single detector can receive the directly scattered light component and the multiply scattered light component of the image during alternate intervals, without the need to move or alter mechanically the field stop between intervals in order to switch between the directly scattered mode and the multiply scattered mode. In such an embodiment, the light component in optical communication with the detector is determined by the illumination source active during a given time interval, rather than by making any physical change to the field stop. For example, illumination from one source location may cause predominantly directly scattered light to impinge on the detector, while another source location may cause predominantly multiply scattered light to impinge on the detector. This switching action can be performed electronically, and thus can be effected much more rapidly than the mechanical switching action associated with altering the geometry of the field stop. In particular, the switching action can occur so rapidly that the retina may move not at all or by only a negligible amount in the blanking interval between the end of the first time interval and the beginning of the second time interval.

In another embodiment, a target having a surface, such as a retina, can be imaged using a scanning technique. For example, light may be directed to a series of two or more points on the target surface, and light remitted by the target points may be separated into directly and multiply scattered light components and individually detected. One image of the target surface can then be generated from the multiply scattered light components, and a second image of the surface can be generated from the directly scattered light components. In such embodiments, the apparatus can include a positioning device for directing light from the light source to a series of two or more selected points on the target surface. In an embodiment, the positioning device moves the light source relative to the subject. This movement includes at least one of moving the light source and moving the subject.

In related embodiments, optical fibers or fiber bundles can be employed to direct light to the target from two or more locations. Two independent light sources can be employed, e.g., one light source for each optical fiber or fiber bundle. Alternatively, one light source can be coupled to two or more independently controllable optical fibers or fiber bundles, whereby the target can be illuminated by each optical fiber or fiber bundle individually. In an embodiment, optical fibers or fiber bundles may simultaneously function as illumination source locations and also as a separation device. In an embodiment, optical fibers or fiber bundles may simultaneously function as illumination source locations, as a separation device, and as a detection system.

An embodiment of the invention provides an endoscope having optical fibers or fiber bundles. The endoscope facilitates characterization of anatomical structures of interest that are internal to a subject such as an organism or other subject having internal structure not readily visualized from outside the confines of the subject. The endoscope may further comprise apparatus for incident light generating, positioning, separating, detecting, and processing as described herein.

The invention further includes an embodiment in which the polarization properties of the remitted light in conjunction with the controlled polarization properties of the illuminating light enable the separation of directly scattered light from multiply scattered light. The polarization of the illuminating light can be controlled by any of several known polarization controllers, such as a rotating polarizer to alter the axes of one or more single illumination sources, a stationary polarization device that alters the polarization state under electronic control, or time-division multiplexing of the illumination source itself. One example of such time-division multiplexing includes the use of multiple sources and a switching circuit, with the illumination directed at the target by a positioning device. Another example is the rapid alteration of the polarization state of a single source such as a Vertical Cavity Surface Emitting Laser or an illumination source with a polarization state generator.

In one instance, the separation of the remitted light may be performed using polarization multiplexing, and the polarization separation device may direct light to two detectors according to the remitted polarization. By controlling the input polarization temporally, the difference in polarization properties between the illuminating light and the remitted light can be calculated. Multiply scattered light has decreased uniformity with respect to polarization, i.e. is depolarized, or has a greater level of random polarization. As a result, it is detected substantially equally in both detectors, independent of the polarization state of the incident light. In contrast, directly scattered light will retain polarization equal or in some other way related to the polarization of the incident light. Therefore, the polarization separation device will communicate the directly scattered light unequally between the two detectors. In this manner, temporal variation of the polarization properties of the illuminating light separation on the basis of polarization properties allows the discrimination of the directly scattered light component from the multiply scattered components.

In a similar embodiment, a polarization state analyzer can be placed in optical alignment before a single detector, and time-division multiplexing can characterize in a near simultaneous manner the polarization properties along specified axes. In general, those skilled in the art will readily generalize these principles of the invention to include multiple sources with different polarization states and/or multiple separation devices and detectors based on the polarization state of the light remitted from the target.

In one practice of the invention, an apparatus as described above can be employed to generate a three-dimensional image or data set of a subject, such as a biological tissue, using the technique of tomography. In this practice, a directly scattered light image and a multiply scattered light image of the subject are obtained for at least two planes of the subject at differing depths by varying the focal plane of the apparatus. The multiply scattered and directly scattered light images can be ordered in series to generate a three-dimensional image or data set from the multiply scattered light images and to generate a three-dimensional image from the directly scattered light images. Thus, in certain embodiments, the apparatus can include a focusing mechanism or control for changing or varying the focal plane of the apparatus.

In general, the data set may contain several components separated based on the light scattering properties of the light remitted from the target, using any of a variety of separation techniques. Further data processing may then be performed on two or more of these components, resulting in a two or three dimensional characterization of the target that includes at least one multiply scattered light component. Therefore, data generated in this way incorporates information from both types of remitted light, rather than only from directly scattered light. This may facilitate observation, comparison, and therapeutic manipulation of subjects. This practice of the invention hence is not limited to the tomographic computations of peak reflectivity derived from only the directly scattered or transmitted light, as described in Dreher et al, 1991.

The localization of target features, in accord with the invention, in either the multiply scattered light component or the directly scattered light component can improve the localization for diagnosis or therapy in a manual or automatic manner. In a two dimensional application in the ophthalmological field, the localization of the central macula or other retinal regions can be difficult due to disease processes that obscure the retinal anatomy. The choroidal rim of the optic nerve head is more readily visualized as a sharp border that is generally round in shape in multiply scattered light than by the features in directly scattered light. The choroidal rim provides an anatomic landmark for the automatic or manual localization of itself or of neighboring structures such as the macula. This landmark is less disturbed by many disease processes, such as age-related macular degeneration, other adult onset or juvenile macular degenerations, presumed ocular histoplasmosis syndrome, retinitis pigmentosa, diabetic retinopathy, ocular hypertension, retinal artery or vein occlusion, or glaucoma, than are the landmarks readily visible in directly scattered light, including retinal blood vessels.

The choroidal rim landmark in multiply scattered light may also be used for rapid positioning, e.g. in examining a large extent of the fundus, such as in the case of screening for choroidal melanoma. The location of the central macula may be found readily, with the practice of this invention, by positioning the illumination source such that the choroidal rim is located at a specified distance and in a specified direction from the target point being examined. As a result, a typical macula may be located in the center of the measurement field or lying below the center. This may be done in an automatic manner. As reported in Chen et al., 1992, for an adult human eye of typical size and shape, the choroidal rim is roughly 3500 microns nasal to the retina and 0 to 1500 microns inferior to it. These typical measurements vary from subject to subject depending upon the size, shape, and refractive power of the eye. In some cases, the retinal vessels or other features that are detected in directly scattered light may add to the accuracy or rapidity of positioning. Additionally, pathological features such as drusen or new blood vessels that are localized in multiply scattered light may be used singly or in combination with other features such as the choroidal rim or retinal landmarks to facilitate diagnosis, treatment, or any other observation, evaluation, or manipulation of the subject, such as guiding the therapeutic beam of a laser.

In the ophthalmological field, pathology may exist in three dimensions, and diagnosis, treatment, and management following treatment can be improved by obtaining the three dimensional characterization of the pathological tissues. Pathological structures, such as the exudative lesions found in age-related macular degeneration, have features that may be readily found using the multiply scattered light component. The pathological retinal elevation that results from fluid accumulation can be quantified, again by practice of this invention, using the directly scattered light component, as in Kunze et al, 1999. Drusen are another pathological structure that are readily located in the transverse directions using multiply scattered light.

Elsner et al, 1998, reported that the axial transfer function of the directly scattered light component was different from the multiply scattered light component, both qualitatively and quantitatively. A combination of the directly scattered light component and multiply scattered light components may further characterize the target for the purposes of diagnosis, treatment, or management following treatment for drusen or exudation.

In the ophthalmological field, the pathology related to age-related macular degeneration is treated with laser photocoagulation or thermal treatment. In one example, new vessels themselves or their associated membrane are photocoagulated. In another example, the entire region of the membrane is treated with thermal therapy, as in transpupillary thermal therapy over a broad region encompassing exudation. A third example is the use of a laser to apply heat treatment for the reduction of drusen, avoiding the fovea and often the drusen themselves. In addition, there is the application of a therapeutic beam with a photoenhancer, as in photodynamic therapy, to treat new vessel membranes. In all these treatments, the pathology may be localized in the multiply scattered light component. Further precision may be obtained by using the directly scattered light component to localize superficial features, which might be smaller and therefore more accurately placed, as well as more familiar from standard clinical methodologies. As many of these treatments are time consuming and may not require expertise in terms of application, as opposed to making the decision for treatment, automatic application of thermal energy may be localized by using the multiply scattered light component.

In such instruments, the data and/or images pertaining to the multiply scattered light component or computations with both the multiply scattered light component may be better utilized by the addition of training or database functions. Such training may include, but is not limited to, describing how to acquire the multiply scattered light component images or data, with or without the near simultaneous comparisons or calculations from the directly scattered light component. Training may also include how to localize the features or choice and to position a diagnostic or therapeutic instrument.

In an embodiment, data and/or images generated by any apparatus, device, or method described herein, or data and/or images generated as a result of practicing any apparatus, device, or method described herein, may be utilized as training materials to teach individuals to operate or to interpret results generated by any apparatus, device, or method described herein.

In an embodiment, the training function includes distance education. The images or data included in the training may be collected at a first location. The training may occur at a second location. The second location may be the same as the first location or may be remote to the first location. In an embodiment, the training images and/or data are generated at a first location, and training occurs at a plurality of training locations. In another practice, the training images and/or data are generated at a plurality of source locations, and training occurs at a plurality of training locations. In a further embodiment, the training images and/or data are generated at a plurality of source locations, and training occurs at a second location.

The transfer of training images or data between the locations may be accomplished by any means of transmittal, including transfer of written or printed documents, transfer of computer storage media, or transmittal of digital information that identifies or defines written or print documents via facsimile. It will be apparent to one of ordinary skill in the art that other communication techniques, systems, and methods are practicable as well, including cable networks, infrared links, short haul modem link or other types of communication link suitable for carrying data between two or more locations, transmittal of electronic data over a network, transmittal of electronic data over a wireless transmittal, or other such means.

In an embodiment, data and/or images generated by any apparatus, device, or method described herein, or data and/or images generated as a result of practicing any apparatus, device, or method described herein may be stored in a database. Examples of data generated include, but are not limited to, normative data, criteria or parameters that indicate abnormal findings, the confidence level by which to judge the abnormality of the findings, change over time, the confidence level by which to judge the amount and direction of change over time, recommended therapeutic treatment, feedback during treatment, success of the treatment, deviation from results expected due to normative data or therapeutic treatment, and quality of the data.

With respect to retinal disease or evaluation, examples include screening for a disease such as age-related macular degeneration, choroidal melanoma, epiretinal membranes, or macular edema; diagnosis for therapeutic treatment; and localization of pathological features before or during treatment.

In an embodiment, training materials may include data and/or images stored in a database. The training may include instruction on the operation of an apparatus or device, or on the performance of a method. In an embodiment, data and/or images from a database may simulate, for training purposes, data gathered from a subject.

The database may include features detected by collection and analysis of multiply scattered light and data generated therefrom. The database may be an integral part of the apparatus or device and corresponding electronic or computer components. The database may be provided in any form during training, collected during training, collected at the location, or transferred from a remote location. These include, and are not limited to, the detection and localization of features afforded by using multiply scattered light. An example pertaining to the retina is the localization of the choroidal rim of the optic nerve head. This function may facilitate the stabilization of an image or the localization of features in or beneath the retina. The success of localization, the position of the features, and relative locations or other features may be stored for future purposes, such as comparison of data collected from other subjects or collected by other means.

In an embodiment, the database is populated with data collected from a processor, generated from a simulation of a target, or derived from an analytical or computational model of a target.

In an embodiment, the database is adapted to distinguish a target or a portion of a target that is abnormal compared to those values stored in the database and considered normal. This consideration may be based upon human judgment, computational evaluation of the data, or by other methods readily apparent to one of skill in the art.

These and other features, aspects, and advantages of the invention will be better understood with reference to the following description and the accompanying drawings in which:

DESCRIPTION OF ILLUSTRATED EMBODIMENTS

The description below pertains to several illustrative embodiments of the invention. Many variations of the invention may be envisioned by one skilled in the art. Accordingly, such variations and improvements are intended to fall within the compass of this disclosure. Thus, the scope of the invention is not to be limited in any way by the disclosure below.

Figure 1:
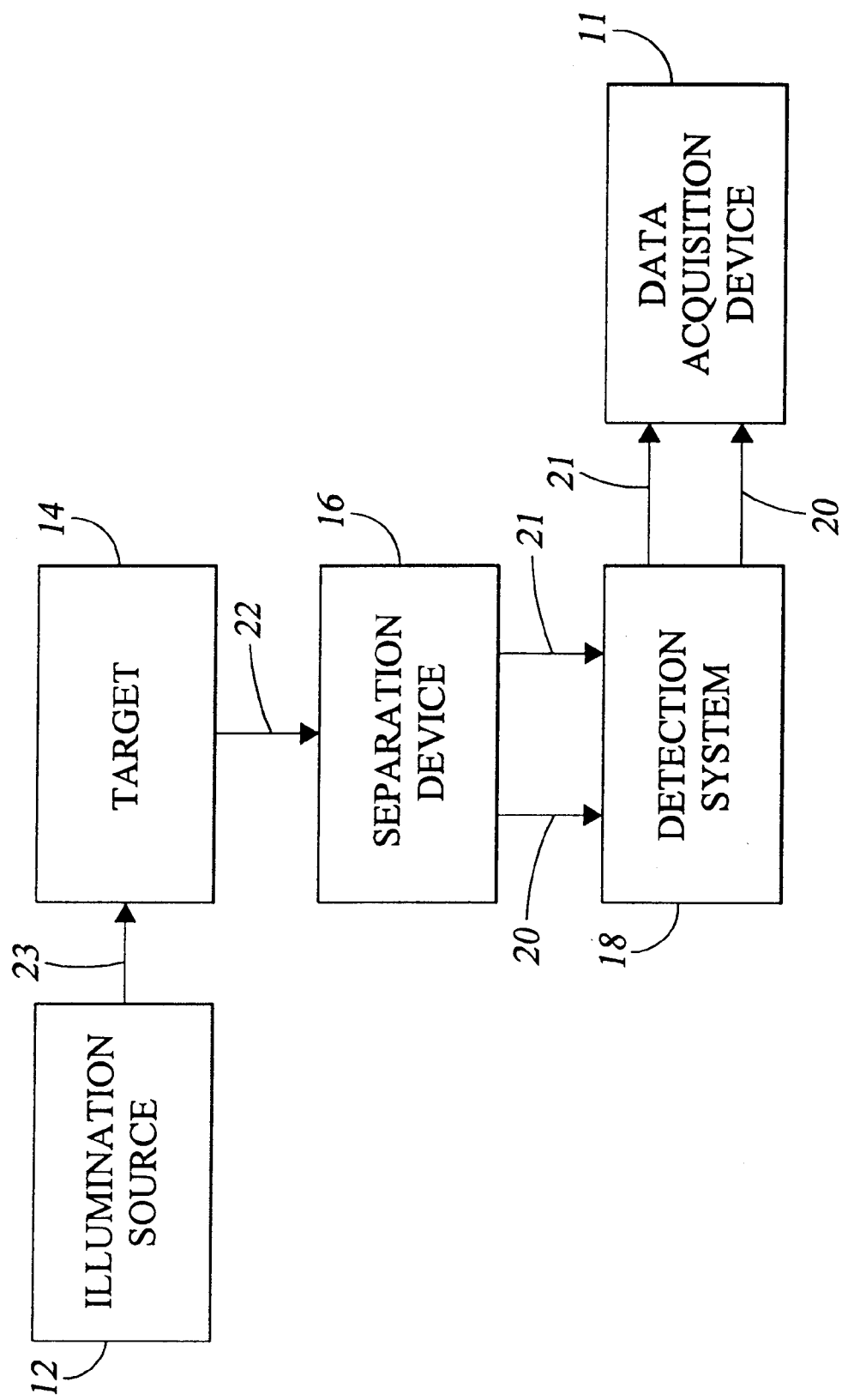
FIG. 1 depicts a functional block diagram of an embodiment comprising an illumination source, in optical communication with a target, which is in optical communication with a separation device, which is in optical communication with a detection system, which is in optical communication with a data acquisition device.

FIG. 1 depicts an optical imaging system according to the invention, and which includes an illumination source 12 for directing incident light 23 at a target 14. An illuminated point on the target remits light to form remitted light 22. The remitted light 22 is directed to a separation device 16, which separates it into its constituent components, i.e., a multiply scattered light component 21 and a directly scattered light component 20. These constituent components are then directed to a detection system 18 that generates an image or data set from each constituent independently of the other.

The two images or data sets thus formed are then passed to a data acquisition device 11. The two images or data sets can then be superimposed, correlated, compared, or in any other way analyzed to determine the spatial relationships between features visible in the directly scattered light image and features visible in the multiply scattered light image, even if no feature is common to both images.

Figure 2:
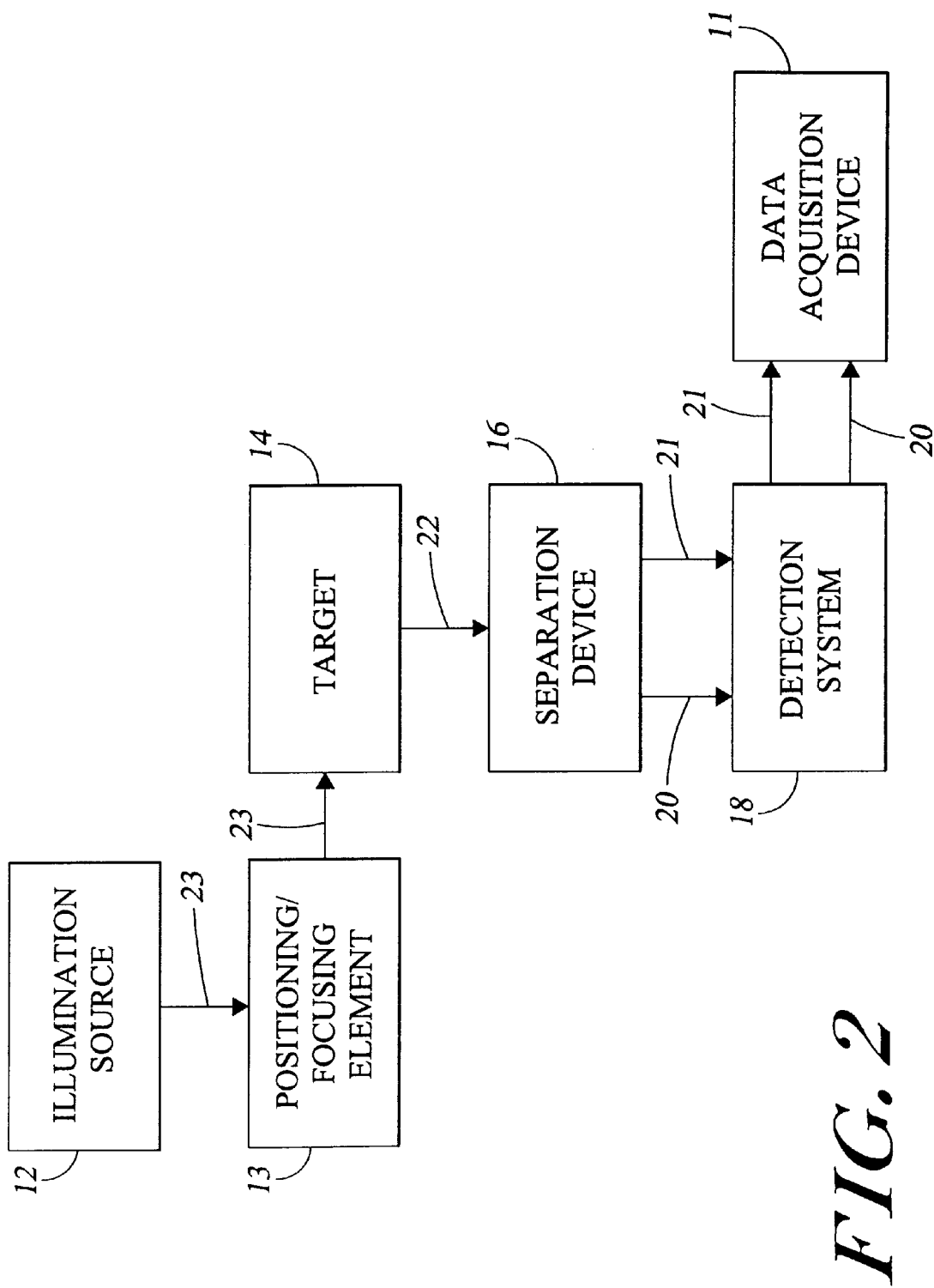
FIG. 2 depicts a functional block diagram of an embodiment related to that depicted in FIG. 1, further comprising a positioning/focusing element interposed between the source and the target.
Figure 3:
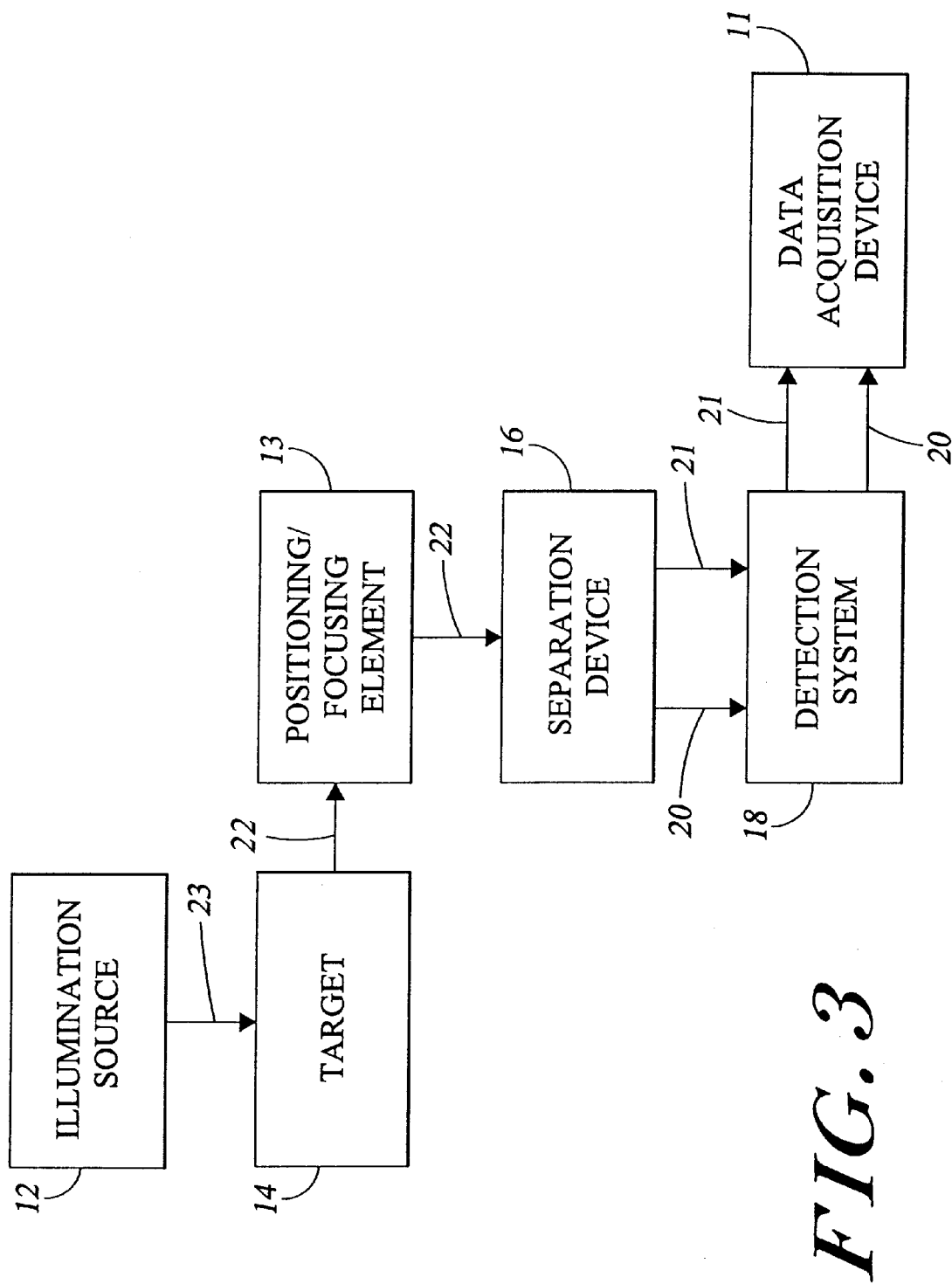
FIG. 3 depicts a functional block diagram of an embodiment related to that depicted in FIG. 1, further comprising a positioning/focusing element interposed between the source and the separation device.
Figure 4:
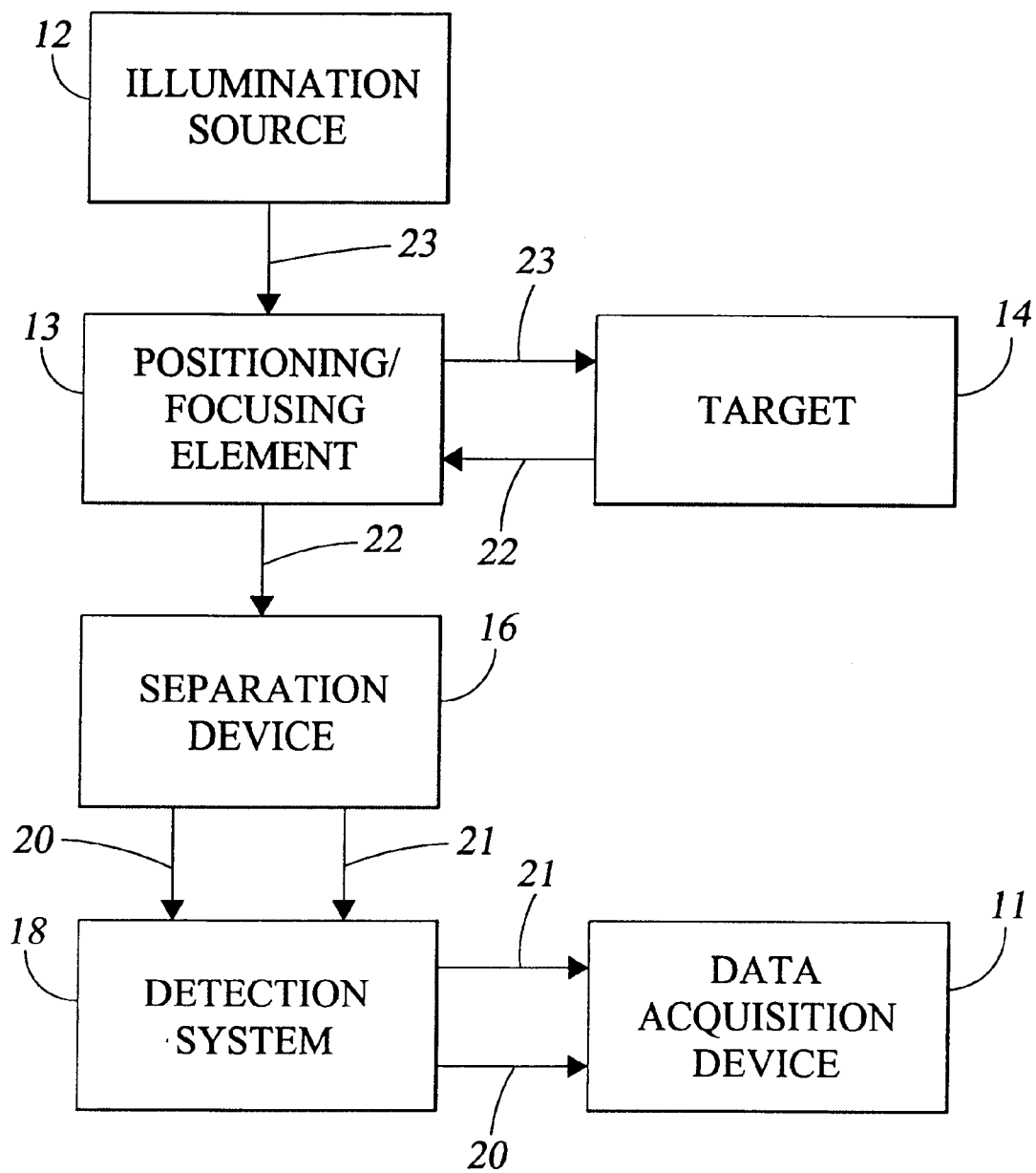
FIG. 4 depicts a functional block diagram of an embodiment related to that depicted in FIG. 1, further comprising a positioning/focusing element interposed between the target and the separation device.

With reference to FIGS. 2, 3, 4, some embodiments may further include a positioning/focusing element 13, enabling such embodiments to perform scanning and tomography. The positioning/focusing element 13 may also be used for target localization, described below. FIG. 2 depicts an embodiment in which incident light 23 emitted from illumination source 12 is directed by the positioning/focusing element 13 to target 14, whereon a series of points may be illuminated in succession. The light remitted 22 by these points is separated into multiply scattered 21 and directly scattered 20 light components, detected, and acquired as described for the embodiment depicted in FIG. 1. As shown in FIG. 3, the positioning/focusing element 13 may also direct the light remitted 22 from the target 14 to the separation device 16. In an embodiment depicted in FIG. 4, the positioning/focusing device 13 may simultaneously direct incident light 23 to target 14 and direct remitted light 22 to the separation device 16.

In an embodiment, a two-dimensional image of a target 14 can be obtained by detecting light remitted 22 from points having different (x,y) coordinates distributed on a plane of the target 14. For example, a series of points of a target 14 can be scanned along a horizontal line, followed by a succession of horizontal lines of points progressively offset along a vertical axis. Imaging data obtained from such a set of points may then be assembled in their respective positions to generate an image. Both multiply scattered light 21 and directly-scattered light 20 may be used to generate images. An embodiment of apparatus according to the invention for scanning a target thus can include a positioning/focusing element 13 disposed as depicted in FIGS. 2, 3, 4.

The positioning/focusing element 13 may also be used to control the focal plane of the target 14 being imaged. In this manner, tomographic imaging of target 14 may be accomplished. In an embodiment, two-dimensional images of multiply-scattered 21 and directly-scattered 20 light from target 14 may be generated as described above for each of a plurality of focal depths. After each two-dimensional image is obtained, the positioning/focusing element 13 may then adjust the focal distance to an adjacent plane. The resulting set of two-dimensional images may then be combined to produce a three-dimensional image. Three-dimensional images obtained from multiply scattered light 21 and directly scattered light 20 may then be separately analyzed or jointly compared, by the data acquisition device, using any analytical technique known to one of skill in the art. In addition, two-dimensional images along any plane in the three-dimensional images may be acquired or computed using techniques known to one of skill in the art.

In one embodiment, a three-dimensional image of a target 14 may be a biological tissue or other material that is at least partially translucent. One exemplary biological tissue is the retina of the eye. In a practice of tomography in accord with the invention, a succession of images of the target is obtained by changing the focal plane of the illuminated point to each of different depths. By ordering these two-dimensional images in series, a three-dimensional image of the target can be constructed. A three-dimensional image can be constructed by imaging successive cross-sections of the target, by imaging successive planes of the target at different depths, or by any other means, as will be apparent to one of skill in the art. An embodiment of apparatus according to the invention for tomographically imaging a target thus can include a focusing control 13 for varying the focal plane of the apparatus.

The techniques of scanning and tomography can be employed concurrently, by scanning the target at each of a series of focal planes, thereby generating a series of two-dimensional images from which a three-dimensional image can be constructed. Various techniques and applications involving scanning, tomography, and combinations thereof are discussed in Elsner et al., *Vision Science and Its Applications,* 1997, 1, SaB1–SaB3; Elsner A. E. et al, *Vision Research* 36, 191–205, 1996; Weinberger et al., *Ophthalmology* 1995, 102, 1445–1449; Dreher et al., *Am. J. Ophthalmol.* 1991, 111, 221–229; *Practical Atlas of Retinal Disease and Therapy,* W. R. Freeman, ed., Lippincott-Raven: Philadelphia, 1997 (esp. Elsner et al., "New Devices for Retinal Imaging and Functional Evaluation", 19–55); Dreher et al., *Applied Optics* 1989, 28, 804–808; Beausencourt et al., *Ophthalmology* 1997, 104, 2018–2029; Beausencourt et al., *Ophthalmology* 2000, 107, 375–385; Kunze et al., *Ophthalmology* 1999, 106, 1830–1840; Zambarakji et al., *Ophthalmology* 1998, 105, 1051–1059; Meyer et al., *Brit. J. Ophthalmol.* 1997, 81, 355–359; Bartsch et al., *Am. J. Ophthalmol.* 1989, 108, 277–287; Elsner et al. *Lasers and Light in Ophthalmology* 1998a, 8, 193–202; Elsner et al. *Investigative Ophthalmol Vis Sci.* 1998b, 39, 2394–2404; Remky et al. *Arch Clin Exp Ophthalmol.* 1999, 237, 897–901; Elsner et al. *Optics Express* 2000, 6, 243–250; Elsner, et al., *Optics Express* 2000, 7, 95–106; Elsner et al., "New devices in retinal imaging and functional evaluation," in *Practical Atlas of Retinal Disease and Therapy,* W. Freeman (ed), Lippincott-Raven, New York, 2nd edition, 19–55, 1998; Chen, J-F., Elsner, A. E., Burns, et al., *Clinical Vision Sciences* 7, 521–530, 1992; Elsner, et al., "Multiply Scattered Light Tomography and Confocal Imaging: Detecting Neovascularization in Age-related Macular Degeneration," in *Trends in Optics,* V. Lakshminarayanan (ed.), Optical Society of America, 35, 379-285, 2000; Elsner, L. Moraes, E. Beausencourt, A. Remky, S. A. Burns, J. J. Weiter, J. P. Walker, G. L. Wing, P. A. Raskauskas, L. M. Kelley. Scanning Laser Reflectometry of Retinal and Subretinal Tissues. Invited chapter in V. Lakshminarayanan (ed.) Trends in Optics, Optical Society of America, 35, 272–278, 2000; Elsner et al., "Detecting AMD with Multiply Scattered Light Tomography," IMSLO proceedings from Bariloche, Argentina, J. Sampaolesi (ed.), In press.

Figure 5:
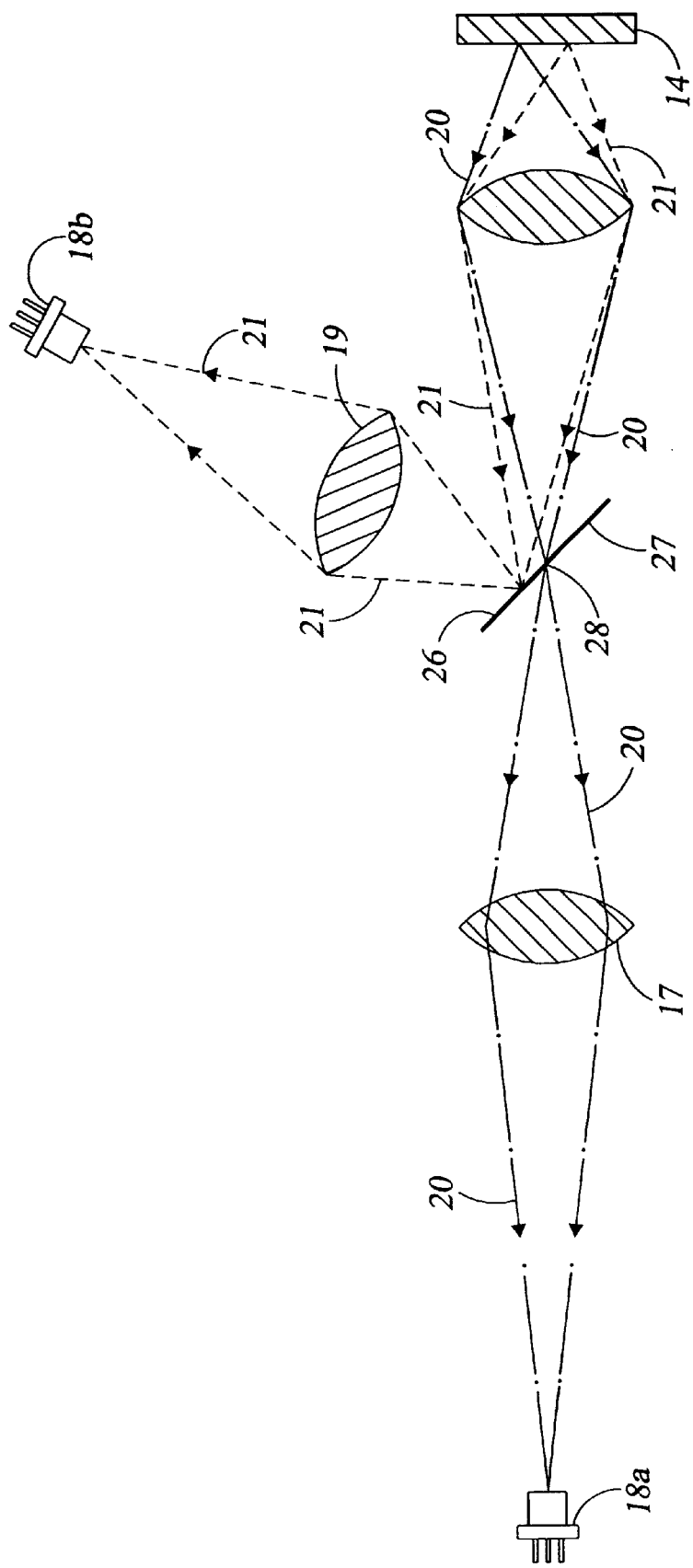
FIG. 5 depicts an embodiment wherein a directly scattered light component and a multiply scattered light component are separated from each other and in optical communication with separate detectors.

With reference to FIG. 5, the separation device 16 of any of the embodiments shown in FIGS. 1, 2, 3, 4 may include a field stop 27 having a pinhole aperture 28 confocal to the illuminated point on the target 14. The face of the field stop facing the target 14 and surrounding the pinhole aperture 28 may form a reflective surface 26 optically aligned to reflect remitted light 22 in the direction of a first optical relay system 19. A second optical relay system 17 may be oriented to receive remitted light passing through the pinhole aperture 28. The detector element 18 in this embodiment may include a first detector 18b in optical communication with the first optical relay system 19 and a second detector 18a in optical communication with the second optical relay system 17.

In operation, a directly scattered light component 20 generated by the illuminated point on the target 14 may impinge on the field stop 27. Because the field stop 27 is confocal to the point on the target 14, the directly scattered light component 20 is focused on the pinhole aperture 28 of the field stop 27. The directly scattered light component 20 may thus pass through the pinhole aperture 28 and enter the second optical relay system 17. The second optical relay system 17 may then direct the directly scattered light component 20 to the second detector 18a.

The path followed by the multiply scattered light component 21 is illustrated by dashed lines in FIG. 5. The multiply scattered light component 21 generated by an illuminated target point may impinge on the field stop 27. Most of the multiply scattered light component 21, however, does not originate from points confocal to the pinhole 28, and consequently does not pass through the pinhole 28. Instead, the multiply scattered light component 21 impinges primarily on the reflective surface 26 of the field stop 27. This reflective surface 26 reflects the multiply scattered light component 21 to the first optical relay system 19, which in turn directs it to the first detector 18b.

It is apparent from FIG. 5 that the foregoing embodiment decomposes the remitted light into its constituent components, namely the directly scattered light component 20 and the multiply scattered light component 21, and renders the constituent components observable simultaneously by directing one component to one detector and the other component to another detector. One of skill in the art will recognize other variations for accomplishing this result. For example, the directly scattered light component can impinge on a reflective region of the field stop and be directed to a first detector, while the multiply scattered light component passes through an optical aperture, e.g. an annular aperture, surrounding the reflective region to a second detector. Alternatively, the directly scattered light component can be received by the end of an optical fiber and transmitted through the fiber to a detector. Other suitable variations that permit the directly scattered light component and the multiply scattered light component to be detected simultaneously can be employed without departing from the spirit and scope of the invention.

Figure 6:
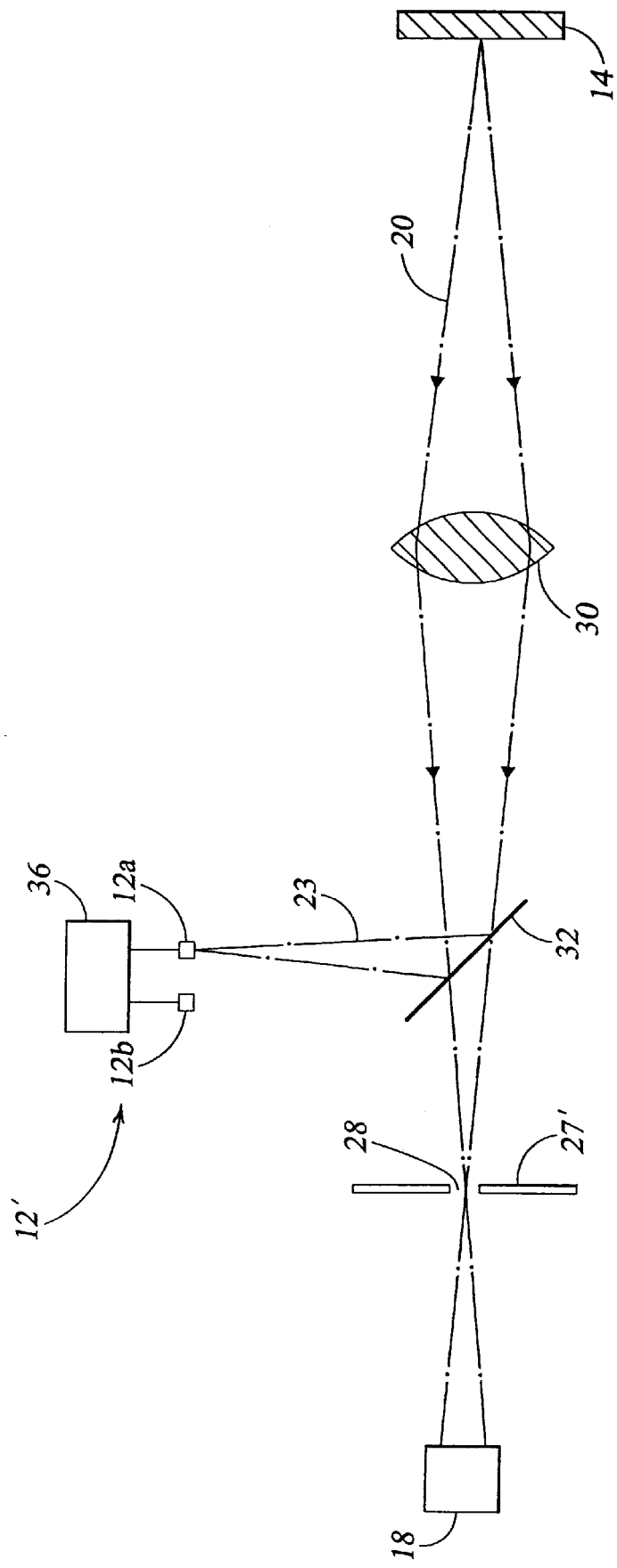
FIG. 6 depicts an embodiment comprising two source positions and wherein activating the first source causes a directly scattered light component to be in optical communication with the detector.
Figure 7:
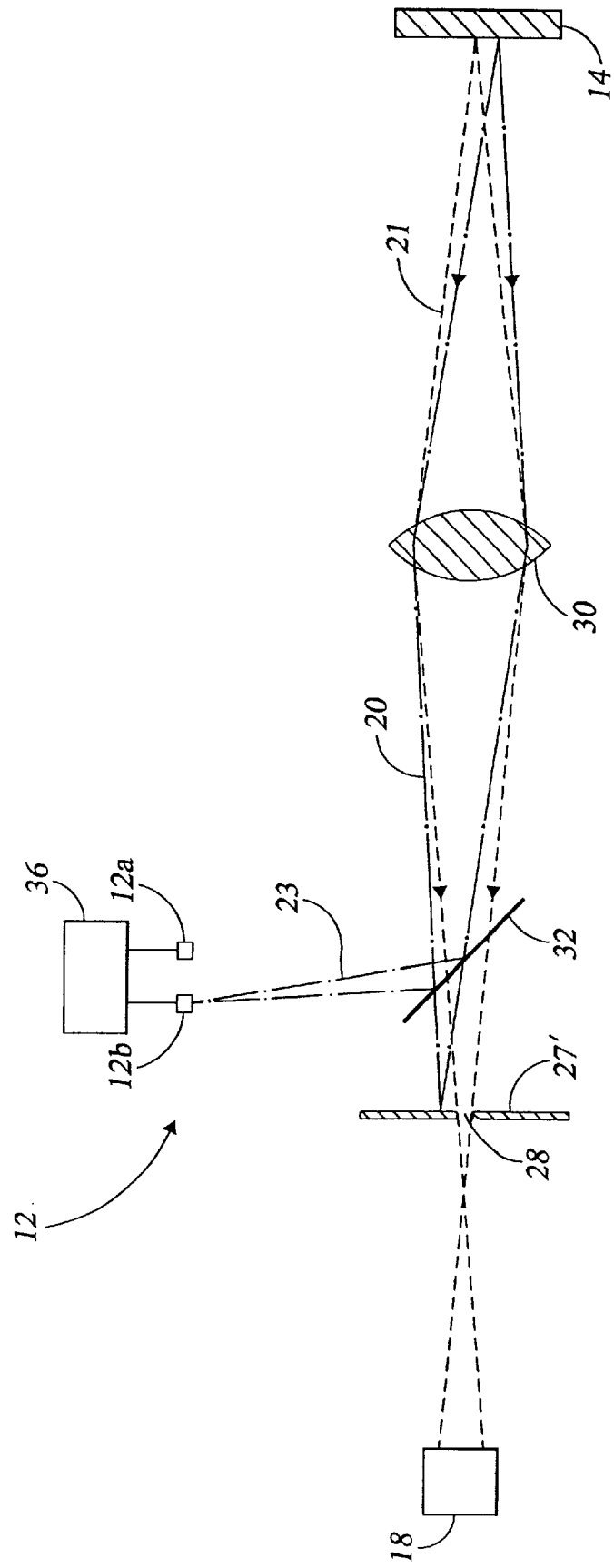
FIG. 7 depicts the embodiment of FIG. 6 and wherein activating the second source causes a multiply scattered light component to be in optical communication with the detector.

Another embodiment of the systems depicted in FIGS. 1, 2, 3, 4 is shown in FIGS. 6 and 7, wherein the detector 18 is disposed to receive light from a target 14 through a pinhole aperture 28 in a field stop 27'.

The illumination source 12' in this embodiment can include a first light source 12a aligned with the optical axis and a second light source 12b transversely displaced from the first light source 12a. The light sources 12a, 12b can be coupled to a switching circuit 36 for switching between the first light source 12a and the second light source 12b. Alternatively, a system that selectively blocks light from one of the two light sources, or a system that causes light from a single light source to be emitted alternately from two adjacent loci, can be employed without departing from the spirit and scope of the invention. The illumination source 12' can be optically coupled to the target by a beam splitter 32 and by an optical relay system 30. In certain embodiments, the first light source 12a and the second light source 12b are independently addressable lasers in a VCSEL (vertical cavity surface emitting laser) array. Although only two light sources are shown, it will be apparent from the following description of the operation of the imaging device that the illumination source 12' can include a greater plurality of light sources. For example, the illumination source may comprise a 3×3 array, configured with the light source 12a employing the central laser, or other illuminating cell, in the source array, the light source 12b employing the eight lasers or cells surrounding the central one. Other configurations will be apparent to one of skill in the art.

In operation, the switching circuit 36 can define a first time interval, during which the light source 12a is on and the light source 12*b* is off, and a second time interval during which the light source 12*b* is on and the light source 12*a* is off. The source 12' thus illuminates the selected target point with light from only one source 12*a* or 12*b* in each time interval.

During the first interval, shown in FIG. 6, the switching circuit activates the first light source 12*a* and deactivates the second light source 12*b*. Light 23 from the first light source reflects off the beam splitter 32 and is directed by the optical relay system 30 to an illuminated point on the target 14. A portion of the light remitted by the illuminated point propagates directly back through the optical relay system 30, thereby forming the directly scattered light component 20. Another portion of the light remitted by the illuminated point in response to the incident field scatters off other points within the target, thereby forming the multiply scattered light component 21 (not shown).

The directly scattered light component 20 passes through the optical relay system 30 and through the beam splitter 32. The optical relay system 30 focuses this directly scattered light at a focal point that is confocal with the illuminated point on the target. During the first interval, this focal point is coincident with the pinhole aperture 28 in the field stop 27'. As a result, during the first interval, the directly scattered light component passes through the pinhole aperture 28 and reaches the detector 18.

After scattering off the last scattering point in the target, the multiply scattered light component 21 also passes through the optical relay system 30. However, unlike the directly scattered light component 20, which originates from a point on the target confocal with the pinhole aperture 28, most of the multiply scattered light component 21 originates from points on the target that are not confocal to the pinhole aperture 28. Thus, the optical relay system 30 focuses this multiply scattered light component 21 at a point on the field stop 27' other than the point at which the pinhole aperture 28 is located. In this way, the field stop 27' blocks the multiply scattered light component 21 from reaching the detector 18.

As shown in FIG. 7, during the second time interval the switching circuit activates the second light source 12*b* and deactivates the first light source 12*a*. Light from the second light source reflects off the beam splitter 32 and is directed by the optical relay system 30 to an illuminated point on the target 14, which remits light comprising a directly scattered light component 20 and a multiply scattered light component 21.

As in the first interval, the directly scattered light component 20 passes through the optical relay system 30, through the beam splitter 32 and comes to a focus at a focal point that is confocal with the illuminated point on the target. However, because the second light source 12*b* is displaced from the first light source 12*a*, this focal point is not coincident with the pinhole aperture 28 in the field stop 27'. As a result, during the second interval, the field stop 27' blocks the directly scattered light component 20.

After scattering off the last scattering point on the target, the multiply scattered light 21 travels back through the optical relay system 30 and through the beam splitter 32. At least a portion of this multiply scattered light 21 originates at a last scattering point on the target that is conjugate with the pinhole aperture 28. This portion of the multiply scattered light 21 is focused at a focal point that coincides with and passes through the pinhole aperture 28 in the field stop 27'. Thus, light passing through the pinhole is primarily multiply scattered light. As a result, during the second interval, the detector 18 detects light that is multiply scattered from that point on the target 14 that is conjugate to the pinhole aperture.

In the apparatus described above, during the first interval, when the first light source is on and the second source is off, the detector receives primarily directly scattered light, while during the second interval, when the second light source is on and the first light source is off, the detector receives primarily multiply scattered light. By rapidly switching between a state in which the first light source is on and the second light source is off and a state in which the second light source is on and the first light source is off, it is possible to view the multiply scattered light component and the directly scattered light component of the image substantially simultaneously.

As described above for the embodiment depicted in FIG. 5, one of skill in the art will recognize variations of the device depicted in FIGS. 6 and 7 that will accomplish this result. For example, the directly scattered light component generated by light from the first light source can impinge on a reflective first region of the field stop that directs the light to a detector, while the multiply scattered light component is received by a second region, such as an opaque or transparent region. Alternatively, the first region can be a facet, e.g., the end, of an optical fiber that transmits the received light through the fiber to a detector. Other suitable variations that permit the directly scattered light component and the multiply scattered light component to be separated and detected substantially simultaneously by alternating the location of the light source that illuminates the target can be employed without departing from the spirit and scope of the invention.

Figure 8:
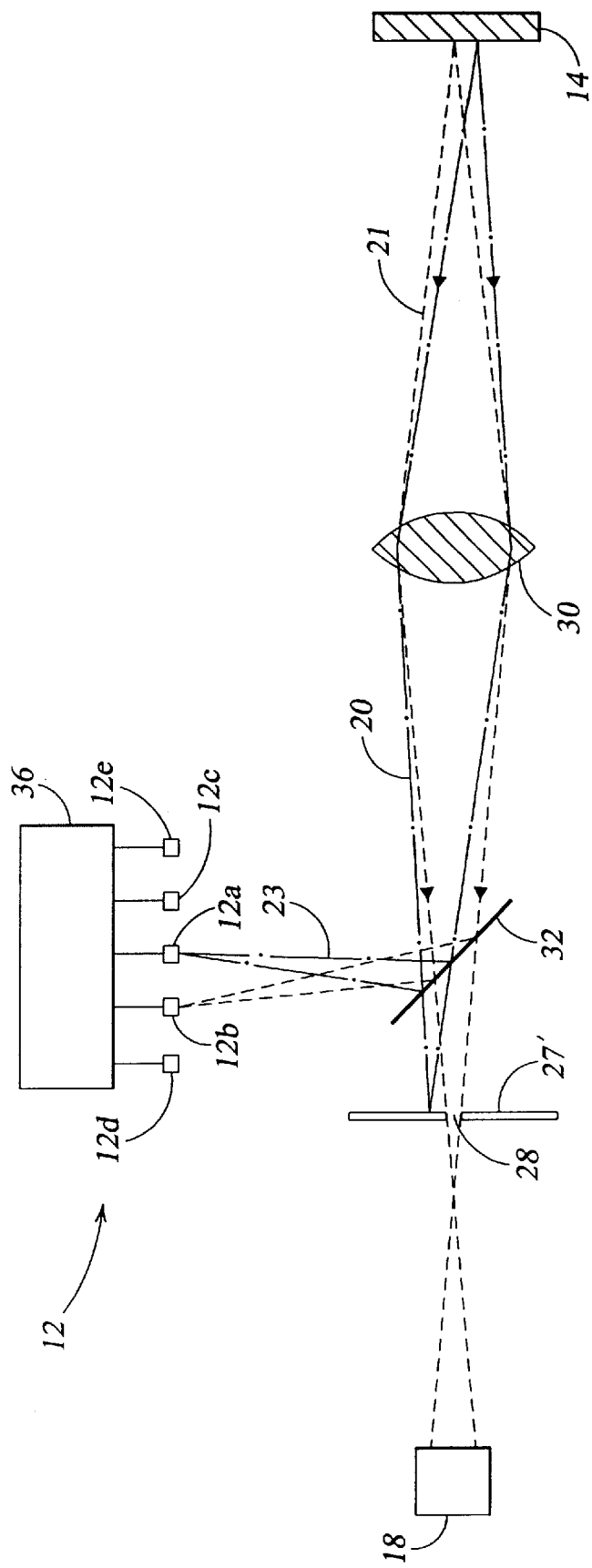
FIG. 8 depicts an embodiment comprising a plurality of source positions.

The sources of illumination may be more than two in number, as shown in FIG. 8. During the first time interval, the switching circuit activates the first light source 12*a* and deactivates the remaining light sources 12*b*, 12*c*, 12*d*, and 12*e*. Each of these sources has a distance between it and the on-axis path of illumination. Light 23 from the first light source reflects off the beam splitter 32 and is directed by the optical relay system 30 to an illuminated point on the target 14. A portion of the light remitted by the illuminated point propagates directly back through the optical relay system 30, thereby forming the directly scattered light component 20. During the second or each of subsequent intervals, the switching circuit activates one or more light sources not activated in the first interval, 12*b*, 12*c*, 12*d*, or 12*e*, and deactivates the first light source 12*a*. Light 23 from one or more of these light source reflects off the beam splitter 32 and is directed by the optical relay system 30 to an illuminated point on the target 14, which remits light comprising one or more multiply scattered light components 21.

In an embodiment, the distance of source 12*b* and 12*c* from the on axis illumination may be less than is the distance of source 12*d* or 12*e*. As a result of this difference in optical path length of the illumination, light detected from the illumination of 12*d* or 12*e* is largely derived from light remitted into a larger volume due to increased number of scattering events or scatter at a greater angle. In a practice of the invention, where the target 14 is an eye fundus or other living tissue, the foregoing increase in scattering indicates a difference in tissue content compared with tissue that scatters light over the smaller volume or lesser angle. Comparison of data collected when illuminating with source 12*a*, as opposed to with sources 12*b* or 12*c*, and additionally compared with illumination from sources 12*d* or 12*e*, and other illumination sources that may be included, can provide a scattering function. Determination of the scattering function facilitates imaging of the target 14, by identifying how incident light 23 is remitted from target 14. Comparison of data collected when illuminating with source 12b as opposed to source 12c, or with source 12d as opposed to source 12e, gives information concerning the direction of scatter.

Figure 9:
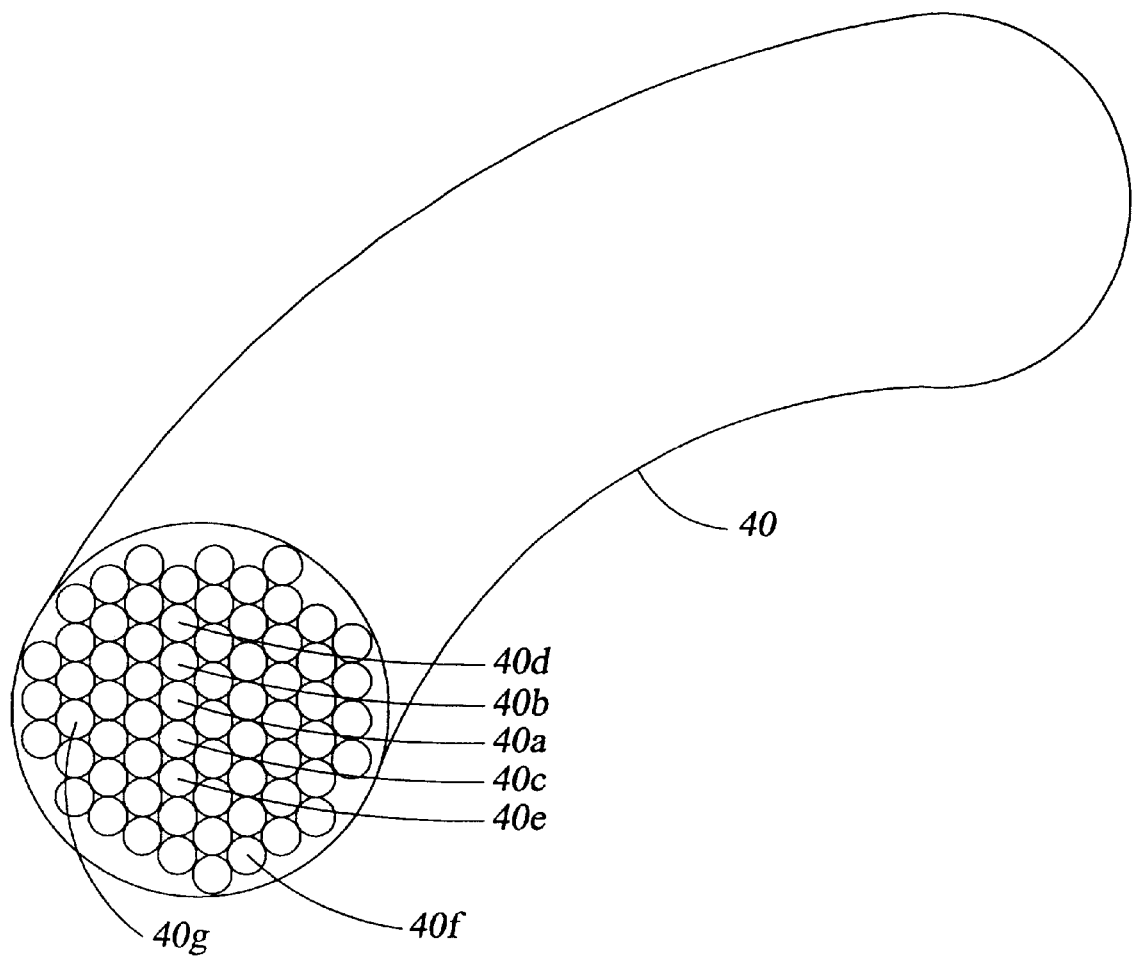
FIG. 9 depicts an optical fiber having a plurality of light conducting members that may function as a plurality of source positions, as a separation device, as a plurality of detectors, or as any combination of these.

With reference to FIG. 9, the illumination source 12 or 12' in any of the preceding embodiments may employ an optical fiber or bundle 40 of optical fibers. A fiber bundle 40 may provide one or more light sources. For example, the source 12' of an apparatus as depicted in FIGS. 6 and 7 can generate illumination by fiber optic transmission from two or more light sources. For example, a first fiber 40a transmitting from a first light source is aligned with the optical axis (not shown) and a second fiber or plurality of fibers 40b, 40c, 40d, and/or 40e. These additional fibers are displaced transversely from the first fiber and constitute a second light source. Remote fibers 40f, 40g may also provide light sources. The switching circuit 36 may provide temporal modulation such that the activation of the first fiber 40a alternates rapidly with the illumination of a second fiber or plurality of fibers. This rapid alternation enables near simultaneous observation of directly scattered light from the first light source and of multiply scattered light from the second light source. Alternatively, one light source can be coupled to two or more independently controllable optical fibers or fiber bundles. Each independent fiber or fiber bundle may be activated by placing it in optical communication with the single light source. With each arrangement, the target 14 is illuminated successively by each independent fiber or fiber bundle. In one illustrative practice, an LCD spatial light modulator can selectively transmit light to two or more predetermined target locations.

An optical fiber bundle 40 as shown in FIG. 9 may also function as the separation device 16 in any of the preceding embodiments. Bundle 40 may be deployed to receive light remitted from target 14. Directly scattered light may be remitted to one fiber 40a or to a selected set of fibers that is preferably centrally located in the bundle. Multiply scattered light may be remitted to other fibers, e.g. 40b, 40c, 40d, and/or 40e that surround fiber 40a. Optical fibers or fiber bundles can direct light remitted from the target, as a separation means having two or more regions. In such embodiments, the fiber bundle can be positioned to receive light remitted from the target such that directly scattered light is received by one or more discrete fibers, while multiply scattered light is received by other fibers. FIG. 1 depicts an optical imaging system according to the invention, and which includes an illumination source 12 for directing incident light 23 at a target 14. An illuminated point on the target remits light to form remitted light 22. The remitted light 22 is directed to a separation device 16, illustratively by way of a fiber bundle as shown in FIG. 9, having two or more elements that separate the remitted light into its constituent components, e.g., a multiply scattered light component elements using fibers 40b, 40c, 40d, and 40e, and a directly scattered light component using fiber 40a. These constituent components are then directed from the separation device 16 to a detection system 18 that generates an image or data set from each constituent independently of the other. The two images or data sets thus formed are then passed to a data acquisition device 11. Thus, a first region of the fiber bundle comprises a subset, optionally a predetermined subset, of the fibers in the bundle, and a second region of the fiber bundle comprises a second subset of the fibers in the bundle, e.g., a subset that does not include fibers of the first subset. Light received by the different subsets can then be separately and independently detected as described above. Similarly, an LCD spatial light modulator can be used as a separation means to direct to a detection system the directly scattered light component and two or more multiply scattered light components.

Figure 10:
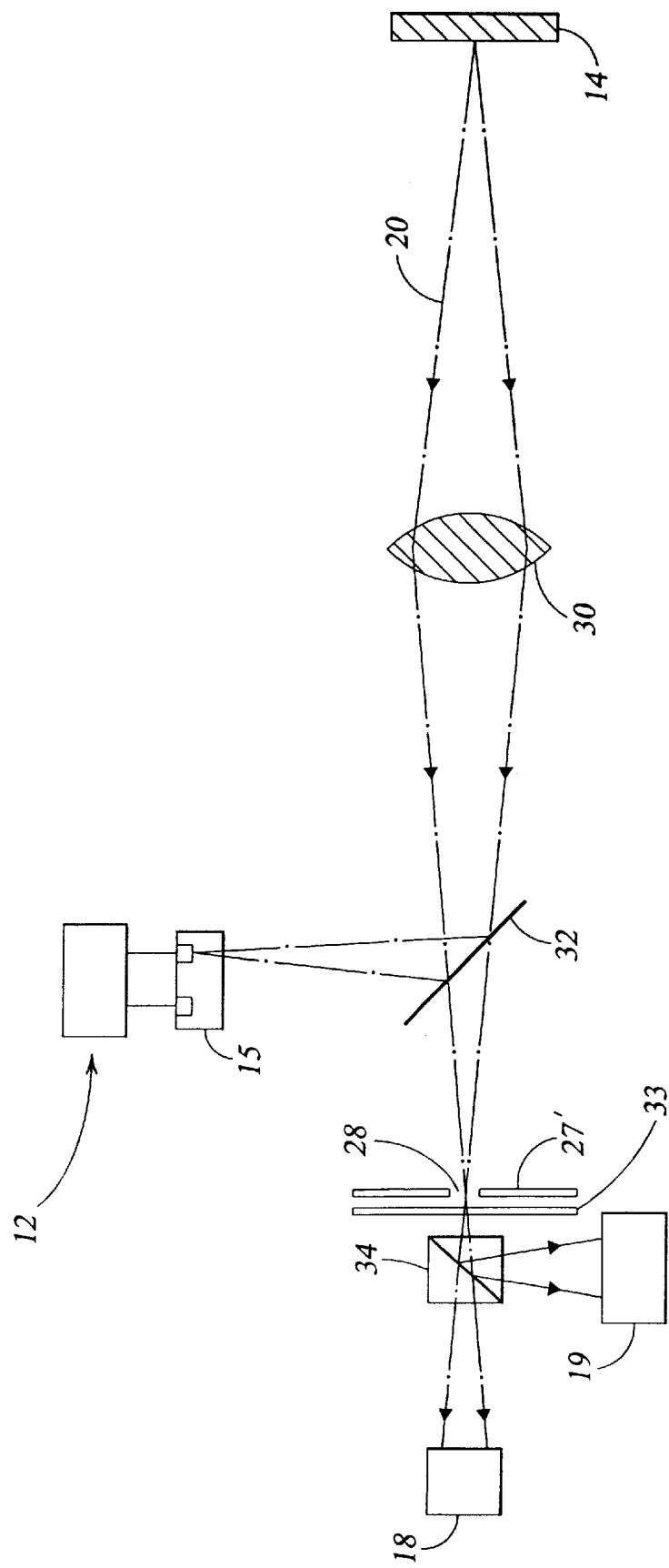
FIG. 10 depicts an embodiment comprising a single illumination source and a separation device having a polarization state generator, a polarization state analyzer, and a polarization separator, wherein the polarization separator is in optical communication with two detectors.
Figure 11:
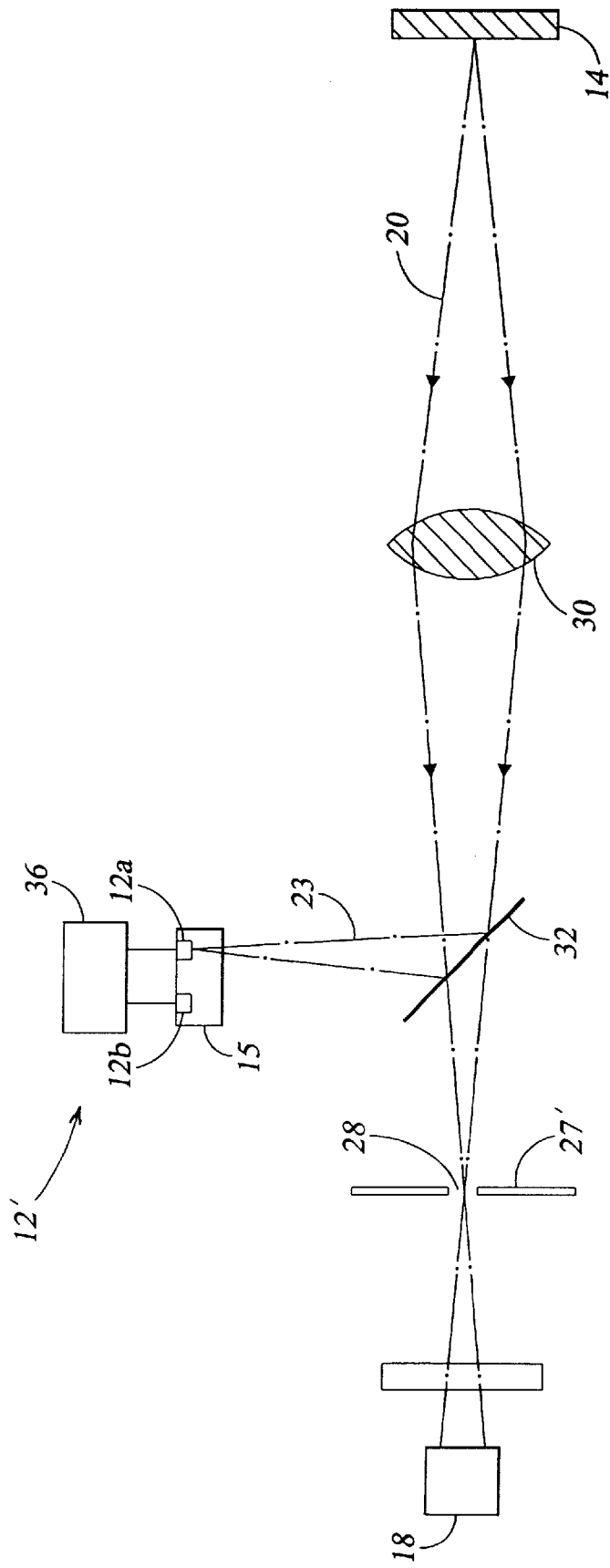
FIG. 11 depicts an embodiment comprising at least two illumination sources and a separation device having a polarization state generator and a polarization state analyzer, wherein the at least two illumination sources are sequentially activated, and the polarization state analyzer is in optical communication with one detector.

FIGS. 10 and 11 depict an optical apparatus, in further accord with the invention, for illumination and detection of light remitted from a target, similar to that shown in FIGS. 6, 7, and 8, and in which the polarization state of the light remitted from the target is detected to separate the directly scattered light component and the multiply scattered light component. In the embodiment shown in FIG. 10, light from the illumination source 12 is passed through a polarization state generator 15 to provide light that is uniformly polarized in a specified manner. The polarized incident light from the illumination source reflects off the beam splitter 32 and is directed by the optical relay system 30 to an illuminated point on the target 14. A portion of the light remitted by the illuminated point propagates directly back through the optical relay system 30. Light remitted from the target, either the directly scattered component 20 or the multiply scattered component 21, passes through the optical relay system 30 and through the beam splitter 32 to a polarization state analyzer 33. The optical relay system 30 focuses the directly scattered remitted light at a focal point that is conjugate with the illuminated point on the target. An optical stop 27' is located in optical alignment with the foregoing elements and has an aperture 28 at that focal point. The directly scattered light and the multiply scattered light pass through the polarization state analyzer 33 prior to being separated by a polarization separator 34. In an embodiment, the returning light passes through a combination of the polarization state analyzer 33 and the polarization separator 34. The separator 34 directs each of the two different remitted components, according to polarization state relative to the incident illumination, to a corresponding detector 18, 19. The detectors produce output signals that are applied to a processor or like data acquisition device 11, as shown in FIG. 1. Rapid alternation of the polarization state of the illumination provides a series of measurements, as does the rapid alternation of the polarization state generator. The data reaching the data acquisition device, shown as 11 in FIG. 1, are further processed. This example includes, but is not limited to, a first remitted light component containing light that retains a greater degree of polarization due to being scattered a relatively fewer number of times prior to reaching the detector and a second remitted light component containing light that retains a lesser degree of polarization due to being scattered a relatively greater number of times. The first component is largely directly scattered light. The image or data resulting from this can be limited to both the position and polarization state of light remitted from the target, which can improve the accuracy of the data or the image quality over directly scattered light data that is not limited in polarization. The second component is largely multiply scattered light, and its uses are similar to those obtained with the preceding examples.

FIG. 11 shows an example of optical imaging apparatus embodying further features of the invention, that operates with polarization as a separation parameter for the directly scattered light component and one or more multiply scattered light components, and that incorporates time-division multiplexing. In the illustrated embodiment, light from an illumination source with two or more source elements 12a, 12b, passes through a polarization state generator 15 to provide selection of uniformly polarized light at specified polarization axes. A switching element 36 switches the source among the illumination source elements. During a first interval, shown in FIG. 11, the switching element 36 activates the first light source 12a and deactivates the second light source 12*b*. Polarized light from the first light source reflects off the beam splitter 32 and is directed by the optical relay system 30 to an illuminated point on the target 14. The directly scattered light component 20 and each multiply scattered light component 21 pass through the optical relay system 30 and through the beam splitter 32. The optical relay system 30 focuses this directly scattered light at a focal point that is conjugate with the illuminated point on the target. This remitted light component hence passes through the aperture 28 of the optical stop 27', as in the instrument of FIG. 10, and is incident on a polarization state analyzer 33 aligned in front of a single detector 18.

In a succeeding second time interval, when the switching element 36 activates the source to illuminate the target point with light from source element 12*b* and not from source element 12*a*, the remitted light component that arrives at the detector 18 is primarily multiply scattered. The directly scattered light and multiply scattered light thus both pass through a polarization state analyzer 33 prior to being directed to the detector 18. The polarization state analyzer is rapidly altered to allow the near simultaneous measurement of light reaching the detector for a specified set of polarization state.

In related embodiments, the illumination source 12 may be a single element or set of elements that can be altered as to its polarization state without a polarization state generator 15. An example is a VCSEL, operated in such a manner that the polarization can be rapidly altered. Such a practice of the invention can employ an illumination source and control device, in place of the polarization state generator 15, the switching circuit 36, and the illumination source 12 of FIGS. 10 or 11. Similarly, in related embodiments, components of the polarization state generator and polarization state analyzer may be combined into common elements and be placed in the optical path between the beam splitter 32 and the target 14. In general, embodiments that operate with polarization as the parameter for separating the directly scattered light component and the multiply scattered light component(s) may include more than two illumination source polarization states and/or more than two analysis polarization states. These embodiments of the invention can be practiced with linearly or circularly polarized light, as well as with other incident polarization states, or a combination thereof.

Figure 12:
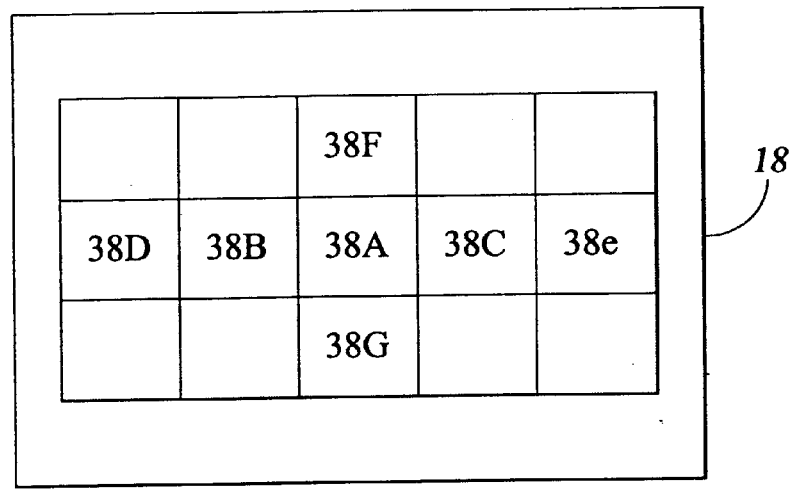
FIG. 12 depicts a detection system having a plurality of detectors.

FIG. 12 depicts an embodiment of the invention in which the detector 18 has a plurality of areas 38*a*, 38*b*, 38*c*, 38*d*, 38*e*, 38*f*, 38*g* disposed in array, analogous to the organization of optical fibers as depicted in FIG. 9. Remitted light is received by the areas 38*a*, 38*b*, 38*c*, 38*d*, 38*e*, 38*f*, 38*g* in a manner analogous to that of individual optical fibers as in FIG. 9, and a processor or similar data acquisition device may perform computations or analysis to compare sets of imaging data acquired by any area 38*a*, 38*b*, 38*c*, 38*d*, 38*e*, 38*f*, 38*g* or any combination thereof.

To improve further the recognition of features of the target, some of which may be poorly detected in one of the two remitted light components, the multiply scattered light component and the directly scattered light component can be utilized in comparative computations to detect and localize features of the target in three dimensions, including direct and iterative computations. In such embodiments, information from one or more two-dimensional series, whether in depth or a lateral series, can be used in computations to provide information about the structures or features within the target volume that is not available in any single image. This information may be obtained from the directly scattered light from the target, or the image formed thereby; the multiply scattered light from the target, or the image formed thereby; or a combination of these two types of light from the target or the images formed thereby. The derived information may be used to detect, more clearly visualize, or localize in either two dimensions or three dimensions structures or features within the target volume. It is not necessary that the structure or feature be visualized in both the directly scattered light component and the multiply scattered light component for such computations and for enhancement of information.

Figure 13:
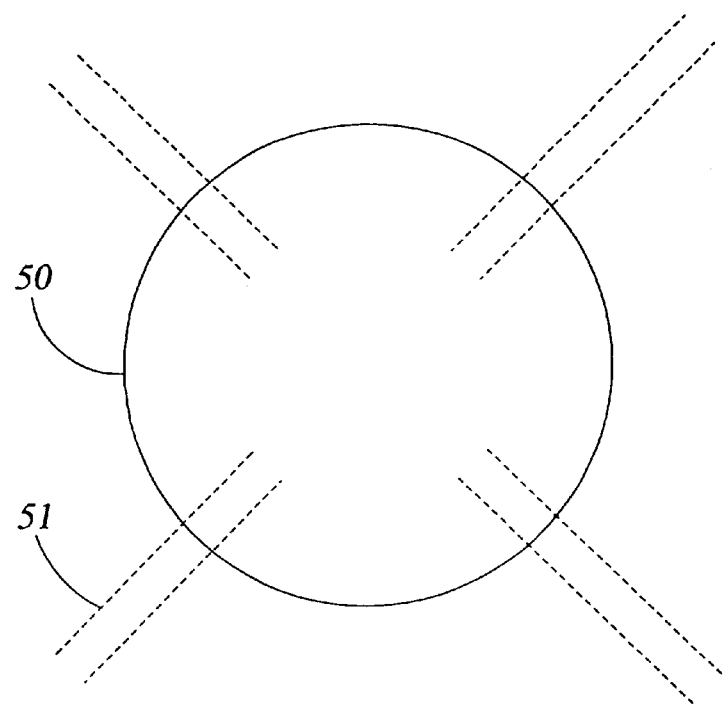
FIG. 13 depicts a schematic view of a choroidal rim and adjacent blood vessels as imaged using multiply scattered light. In a practice of the invention.

FIG. 13 illustrates this feature of the invention and shows the recognition of a target feature 50 that is imaged with multiply scattered light, to position this or another feature, either manually or automatically, for further optical imaging of the latter feature. In this example is depicted the choroidal rim 50 of the optic nerve head, which lies beneath the highly remittive retina, and is therefore better visualized and localized in the transverse direction. The data at the detector is passed to a data acquisition device 11 as in FIGS. 1–4 for further processing. A computer or device with a central processing unit locates the border and the optic nerve head. This feature is positioned in the field of view or in the target location, in an accurate and automatic manner by use of the three dimensional positioning element 13 as shown in FIGS. 2, 3, and 4.

Further, another feature of the target shown in FIG. 13, in this example a retinal blood vessel 51, is visualized to some extent in the multiply scattered light component, as indicated by a dashed line. The additional use of the directly scattered light component, in an at least near simultaneous manner described above to localize the other feature, which is imaged more distinctly in the directly scattered light component, a retinal blood vessel 51 in this example, further specifies the target accurately in the transverse direction. This target feature, which typically has a narrow axial transfer function and a single peak, provides for accurate positioning in the axial direction directly by the determination of either maximum contrast or overall signal in the plane of focus at this location.

Figure 14:
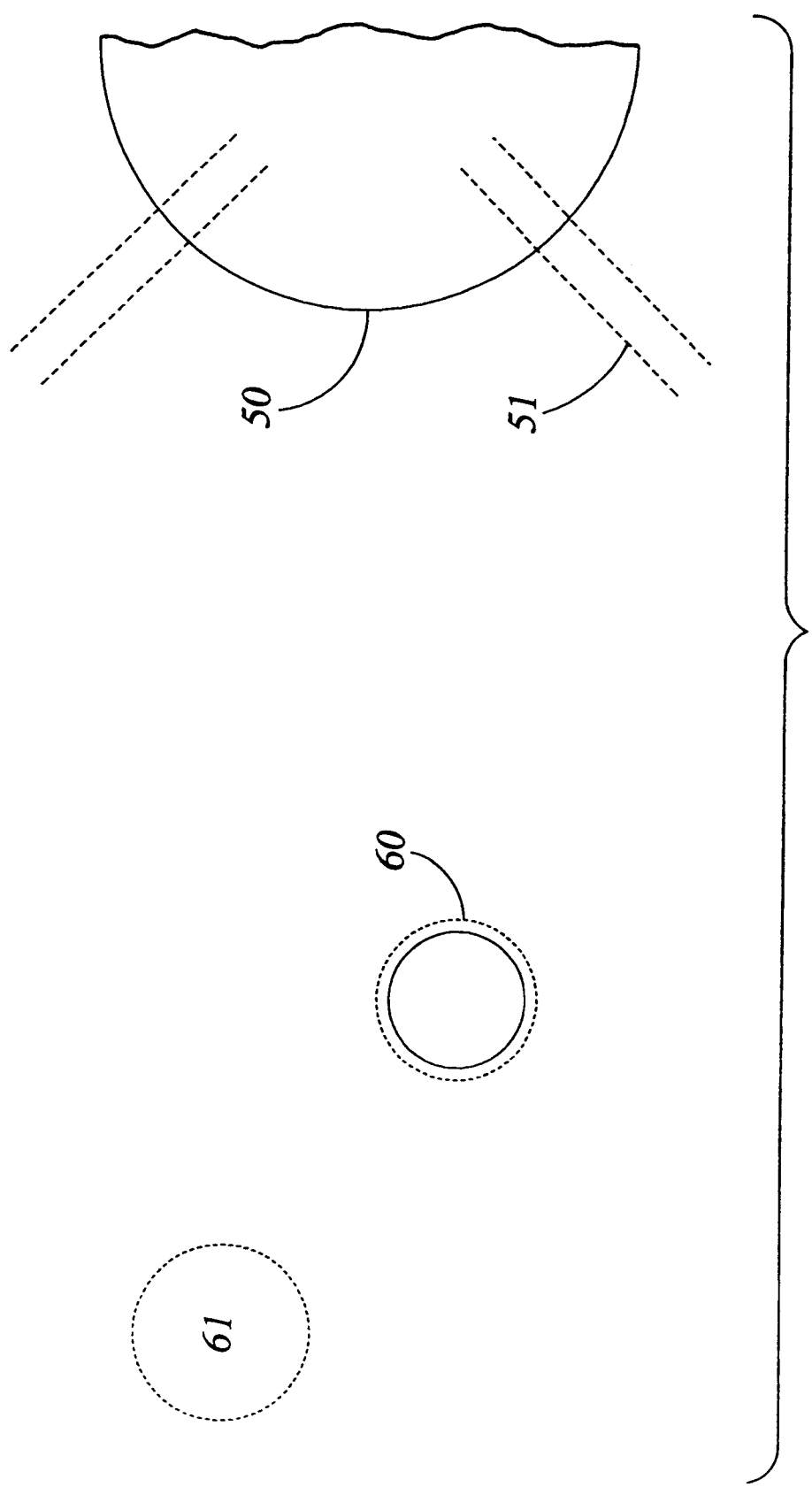
FIG. 14 depicts a schematic view of a macular pathology located with reference to a choroidal rim and retinal blood vessels imaged using multiply scattered light in a practice of the invention.

FIG. 14 shows the choroidal rim of the optic nerve head 50 and the retinal vessel 51 at the right side to indicate that another aiming or target position is desired for the diagnostic or therapeutic device. In one practice as illustrated, the choroidal rim of the optic nerve head 50 is localized with a multiply scattered light component. A previously determined calculation based on the three-dimensional distances of the target is used to aim the diagnostic or therapeutic device to a new position, in this example to aim at the macular pathology 60 using the three-dimensional positioning device 13 of the instrument shown in FIGS. 2, 3, and 4. The positioning device 13 enables the selective positioning of either the target or the diagnostic or therapeutic device or both, in the instrument field of view.

Alternatively, the macular pathology 60 can be visualized with a multiply scattered light component with or without reference to the first feature 50 or to the features seen better in the directly scattered light components, such as vessel 51. An example is a choroidal new membrane in age-related macular degeneration being localized and adjusted in relative viewing position with respect to a treatment device for photocoagulation, photodynamic therapy, transpupillary thermal therapy, radiation therapy, or any other therapeutic or diagnostic manipulation of the target. In photodynamic therapy, transpupillary therapy, or radiation therapy, extended exposure is necessary but the accuracy of positioning allows for error typically greater than the width of a feature such as the imaged vessel 51.

In the foregoing example of the choroidal rim of the optic nerve head, the position of one or more of such retinal vessels defines a plane of focus. This belongs to a class of features for which there typically is the narrowest axial transfer function and a single peak. The foregoing example provides for the accurate positioning in the axial directly by the determination of either maximum contrast or overall signal in the plane of focus at this location. The plane of the retina at the macula, without pathology, lies somewhat below the plane of focus at the retinal vessels. The three-dimensional positioning or focusing element, i.e. the positioning/focusing element 13 of FIGS. 2–4, is then used to visualize the structures in the macula according to their respective positions. The plane of focus of the retina in the macular region can be elevated when there are features beneath the retina that elevate the retina. The resulting axial transfer function may no longer be narrow or have a single peak. One strategy for focusing is to localize a region near the macula which lacks features of high contrast in the multiply scattered light component area 61 in FIG. 14, and to use this localization for a plane of reference for aiming the diagnostic or therapeutic device. Further computations of desired planes for aiming the diagnostic or therapeutic device may use either this plane or the one from the optic nerve head.

The positioning illustrated in FIG. 14 may be performed a series of times to make a montage of a larger area or provide a map for the aiming with respect to the target during diagnosis or treatment and report of the results. This practice of the invention employs the imaging results from the multiply scattered light component(s) alone or in combination with the results from the directly scattered light component. In one practice, a computer may store the initial position reported by the data acquisition device 11, e.g. FIGS. 2, 3, and 4, then moves the position of the target with respect to the device by means of the three dimensional positioning/focusing device 13. New data are acquired, and the target is moved again with respect to the diagnostic or therapeutic device by the positioning or focusing device 13. The results of the data may guide the next step or a precalculated series of steps may be made.

In certain embodiments, additional separation of directly scattered light from multiply scattered light can be achieved, for example, with the techniques described by Benedetti et al., U.S. Pat. No. 6,016,367.

EXAMPLE

Separating Sub-retinal and Retinal Structures Using Polarimetric Imaging

Methods: 22 eyes of 12 subjects with a spherical equivalent less than 6 D were tested. Scanning laser polarimetry images were obtained using a commercial scanning laser polarimeter (GDx, LDT, San Diego, Calif.). Two detectors simultaneously measure light returning from the retina that is either polarized parallel or perpendicularly to the illumination. Twenty sequential paired images, each at a different input polarization, are obtained. Typically the data are used to determine nerve fiber layer thickness. Custom software was developed (MatLab, Mathworks, Natick, Mass.) to combine information from all 40 images, using a linear birefringence model for the combined effects of cornea and nerve fibers to compute, pixel by pixel, separate images that correspond to 1) the amount of parallel polarized light at each retinal location for all angles, 2) the amount of perpendicularly polarized light, 3) the amount of depolarized light, 4) the reflectance for randomly polarized light, and 5) the distribution of birefringence in the retinal image. We computed the contrast of features in each type of image. Data were corrected for variations in instrument polarization properties at each pixel, and relative gains of the detectors.

Results: As hypothesized, the contrast of deeper retinal features such as drusen and peripapillary atrophy were increased in the depolarized light images. For instance, the contrast of small drusen was higher ($p<0.001$) in the depolarized light images than polarization retaining images by 1.3 times to more than 10 times. The polarization modulation image emphasized elements that are birefringent, such as the NFL.

Conclusions: Scanning laser polarimetry allows imaging of retinal structures based on their physical properties, improving quantification of deeper retinal layers, typically obscured by the superficial layers such as the NFL and photoreceptors.

While the invention has been disclosed in connection with the embodiments shown and described in detail, various equivalents, modifications, and improvements will be apparent to one of ordinary skill in the art from the above description. Such equivalents, modifications, and improvements are intended to be encompassed by the following claims.

We claim:

1. An optical imaging apparatus comprising
    a lighting system to illuminate a point of a target and generate at least one multiply scattered light component and a directly scattered light component in response to the illumination,
    a positioning element for varying the point of the target illuminated by the lighting device among a plurality of points of the target,
    a separation device to isolate the directly scattered light component and different ones of said multiply scattered light components from each other,
    a detection system to detect at least substantially simultaneously the directly scattered light component and the at least one multiply scattered light component, and
    a processor for generating a first set of image information from the directly scattered light component and a second set of image information from the at least one multiply scattered light component.

2. The imaging apparatus of claim 1, further comprising a focusing control element for varying a focal plane of the apparatus.

3. The imaging apparatus of claim 1, wherein the detection system comprises a first detector for detecting the directly scattered light component and a second detector for detecting the at least one multiply scattered light component.

4. The imaging apparatus of claim 1 wherein said positioning element varies said point of said target in response to at least one of said sets of image information.

5. The imaging apparatus of claim 1, wherein the lighting system comprises a laser.

6. The imaging apparatus of claim 1, wherein the lighting system comprises at least one optical fiber.

7. The imaging apparatus of claim 1, wherein the detection system individually detects the directly scattered light component and the at least one multiply scattered light component.

8. The imaging apparatus of claim 1, wherein different ones of said multiply scattered light components each has a scattering angle and a distance from said target, and
    wherein the separation device isolates the different ones of said multiply scattered light components from each other in response to at least one of said scattering angle and said distance.

9. The imaging apparatus of claim 1, wherein said lighting system illuminates said point of said target with light having a selected polarization, and said separation device isolates said directly scattered light component from said at least one multiply scattered light component in response to polarization relative to said selected polarization.

10. The imaging apparatus of claim 1, wherein said lighting system includes a polarization state generator and illuminates said point of said target with incident light having a selected incident polarization state, and wherein said separation device includes a polarization state detector and produces said directly scattered light component in response to remitted light having a first polarization state relative to said incident polarization state, and produces said at least one multiply scattered light component in response to remitted light having a second polarization state relative to said incident polarization state.

11. The imaging apparatus of claim 1, wherein the lighting system comprises a plurality of source locations and a switch for selectively activating different ones of said source locations and for sequentially illuminating said target by said different ones of said source locations during a plurality of time intervals.

12. The imaging apparatus of claim 11, wherein the light remitted from said target as a result of sequential illumination from different ones of said source locations is received sequentially by said detection system during said plurality of time intervals.

13. The imaging apparatus of claim 1, wherein the separation device includes a first region optically conjugate to the illuminated target point, the first region selecting the directly scattered light component, and a second region adjacent to the first region, the second region selecting the at least one multiply scattered light component, and the detection system includes a first detector in optical communication with the first region.

14. The imaging apparatus of claim 13, wherein the detection system further includes a second detector in optical communication with the second region.

15. The imaging apparatus of claim 13, wherein one said region comprises an aperture and the other said region comprises a reflective surface.

16. The imaging apparatus of claim 13, wherein at least one of said first and second regions comprises a facet of at least one optical fiber.

17. The imaging apparatus of claim 1 wherein said processor further generates one or more further sets of image information from different ones of said multiply scattered light components.

18. The imaging apparatus of claim 1, wherein the lighting system includes a first light source and a second light source displaced from the first light source, and said separation device includes a first region optically conjugate to the first light source and a second region adjacent to the first region.

19. The imaging apparatus of claim 18, wherein each of the first and second light sources comprises a laser.

20. The imaging apparatus of claim 18, wherein each of the first and second light sources comprises a laser in an array of vertical cavity surface emitting lasers.

21. The imaging apparatus of claim 18, further comprising a switch for alternating between a first interval during which said target receives light from said first light source but not from said second light source, and a second interval during which said target receives light from said second light source but not from said first light source.

22. The imaging apparatus of claim 1, wherein the lighting system emits light from a first locus and from a second locus adjacent to the first locus, and wherein the lighting system includes a switch for alternating between a first state wherein the lighting system emits light only from the first locus and a second state wherein the lighting system emits light only from the second locus, and the separation device includes a first region optically conjugate to the first locus with respect to only one of said light components.

23. The imaging apparatus of claim 1, wherein said processor generates a set of scattering function data from the at least one multiply scattered light component.

24. The imaging apparatus of claim 1, wherein the imaging apparatus is disposed within an endoscopic device.

25. A method for optical imaging, comprising directing incident light successively to a first series of points of a target, whereby each point of the series of points remits light, separating the light remitted by each point of the first series of points into a directly scattered light component and at least one multiply scattered light component, detecting the directly scattered light component and the at least one multiply scattered light component of the light remitted by each point of the first series of points, and generating a first set of image information from the directly scattered light component and a second set of image information from the at least one multiply scattered light component.

26. The method of claim 25 wherein said generating further generates one or more further sets of image information from different ones of said multiply scattered light components.

27. The method of claim 25, further comprising repeating said directing, separating, detecting, and generating for a second series of points located at a different depth from the surface of the target than the first series of points.

28. The method of claim 25, wherein said directing is responsive to at least one said set of image information.

29. The method of claim 25, wherein said detecting of the directly scattered light component and of the at least one multiply scattered light component includes detecting the directly scattered light component with a first detector and at least substantially simultaneously detecting the at least one multiply scattered light component with at least one additional detector.

30. The method of claim 25, wherein said directing of incident light includes directing light from a laser.

31. The method of claim 25, wherein said directing of incident light includes directing light from a facet of at least one optical fiber.

32. The method of claim 25, wherein said detecting of the directly scattered light component and of the at least one multiply scattered light component includes individually detecting the directly scattered light component and the at least one multiply scattered light component.

33. The method of claim 25, wherein said directing of incident light includes directing incident light with a selected polarization, and said separating of remitted light includes responding to polarization relative to the selected polarization.

34. The method of claim 25, wherein
said separating includes
selecting the directly scattered light component with a first region optically conjugate to the illuminated point, and
selecting the at least one multiply scattered light component with a second region adjacent to the first region, and
said detecting includes
detecting the directly scattered light component with a first detector in optical communication with the first region, and
detecting the at least one multiply scattered light component with a second detector in optical communication with the second region.

35. The method of claim 25, further comprising guiding a medical device with reference to at least one set of image information.

36. The method of claim 25, further comprising
employing the at least one set of image information to train an operator to recognize features present in the at least one set of image information.

37. The method of claim 25, wherein
said directing of incident light includes providing
a first light source and
a second light source displaced from the first light source, and
said separating includes
illuminating a point of the target with the first light source,
receiving the directly scattered light component within a region optically conjugate to the first light source,
illuminating the point of the target with the second light source, and
receiving the at least one multiply scattered light component within said region.

38. The method of claim 37, further comprising switching between a first interval during which the first light source is turned on and the second light source is turned off and a second interval during which the second light source is turned on and the first light source is turned off.

39. A method for tomographically imaging a target comprising
directing incident light to a target, thereby generating at least one multiply scattered light component and a directly scattered light component,
separating the directly scattered light component from the at least one multiply scattered light component with a separation structure having a first focal plane,
detecting the directly scattered light component and the at least one multiply scattered light component, and
generating a first image from the directly scattered light component and a second image from the at least one multiply scattered light component,
changing the focal plane of the separation structure to a different second focal plane, and
repeating said directing, separating, detecting, and generating for said second focal plane.

40. The method of claim 39, wherein said detecting of the directly scattered light component and of the at least one multiply scattered light component includes detecting the directly scattered light component with a first detector and at least substantially simultaneously detecting the at least one multiply scattered light component with a second detector.

41. An imaging device comprising
a light source to emit light to illuminate a point of a target and generate a multiply scattered light component and a directly scattered light component in response to said illumination,
a scanning element to direct the light emitted by the light source to a series of points of the target in succession,
a reflective filter having an aperture, and being in optical communication with the light source,
an optical system for focusing light directly scattered by the point of the target on the aperture,
a first detector positioned to receive light transmitted through the aperture and generate a first image therefrom, and
a second detector positioned to receive light reflected by the filter and generate a second image therefrom,
whereby the at least one multiply scattered light component and the directly scattered light component are detected substantially simultaneously.

42. The imaging device of claim 41, further comprising a focusing element for varying a focal plane of the optical system.

43. An imaging device for separating light received from a target into a multiply scattered light component and a directly scattered light component, the device comprising
a lighting system, comprising a first light source and a second light source displaced from the first light source, to illuminate a point of the target and generate a multiply scattered light component and a directly scattered light component,
a scanning element to vary the point of the target illuminated by the lighting system,
a filter having an aperture to separate the directly scattered light component from the at least one multiply scattered light component,
an optical system for focusing light remitted by the point of the target on the aperture,
a detector positioned to receive light passing through the aperture and generate a first image from the directly scattered light component and generate a second image from the at least one multiply scattered light component,
whereby the directly scattered light generated by the first light source is received by the detector, and the directly scattered light generated by the second light source is blocked by the filter.

44. The imaging device of claim 43, further comprising a focusing element for changing a focal plane of the optical system.

45. The imaging device of claim 43, further comprising a light control system for alternating between a first condition wherein the target is illuminated by the first light source but not by the second light source, and a second condition wherein the target is illuminated by the second light source but not by the first light source.

46. An imaging apparatus for separating light received from a target into at least one multiply scattered light component and a directly scattered light component, the apparatus comprising
illumination means for directing incident light to a point of the target, thereby generating a multiply scattered light component and a directly scattered light component,
separation means for separating the directly scattered light component from the at least one multiply scattered light component, detecting means in optical communication with the separating means for detecting the directly scattered light component and the at least one multiply scattered light component, positioning means for varying the point of the target illuminated by the illumination means among a plurality of points of the target, and data processing means for generating a first set of image information from the directly scattered light component and a second set of image information from the at least one multiply scattered light component.

47. The imaging apparatus of claim 46, further comprising focusing means for varying a focal plane of the separation means.

48. A method for separating light received from a target into at least one multiply scattered light component and a directly scattered light component, the method comprising directing light from a first light source onto a point of a target and thereby generating at least one multiply scattered light component and a directly scattered light component, separating the directly scattered light component from the at least one multiply scattered light component with a filter having an aperture, detecting the directly scattered light component and the at least one multiply scattered light component with a light detection system, varying the point of the target receiving light among a plurality of points of the target, and generating a first set of image information from the directly scattered light and a second set of image information from the at least one multiply scattered light.

49. The method of claim 48, wherein separating comprises reflecting the at least one multiply scattered light component from a reflective surface of the filter and transmitting the directly scattered light component through the aperture of the filter, and detecting comprises detecting the directly scattered light component with a first detector positioned to receive light transmitted by the aperture of the filter and substantially simultaneously detecting the at least one multiply scattered light component with a second detector positioned to receive light reflected by the filter.

50. The method of claim 48, further comprising directing light from a second light source onto the target, whereby light projected from the first light source generates directly scattered light that passes through the aperture of the filter, and light projected from the second light source generates directly scattered light that is blocked by the filter.

51. The method of claim 48, further comprising alternating between a first condition wherein the point of target receives light from the first light source and not from the second light source, and a second condition wherein the point of the target receives light from the second light source and not from the first light source.

52. An optical imaging apparatus comprising a lighting system to illuminate a point on a target and to generate therefrom various scattered light components, a positioning element for varying the point of illumination on the target a separation device to isolate a directly scattered light component and at least one multiply scattered light component from each other, and processor for generating a first set of data from the directly scattered light component and a second set of data from the at least one multiply scattered light component.

53. The imaging apparatus of claim 52, wherein said processor is adapted to generate a set of scattering function data from at least two of said various scattered light components.

54. The imaging apparatus of claim 52, wherein said at least one multiply scattered light component has a scattering angle and a distance from said point, and wherein the separation device isolates said at least one multiply scattered light component in response to at least one of said scattering angle and said distance.

55. The imaging apparatus of claim 52, wherein the processor is adapted to couple at least a portion of at least one said set of data to a training function.

56. The imaging apparatus of claim 52, wherein said lighting system illuminates said point with light having a series of selected polarizations, and wherein each of said various scattered light components has a polarization state, and wherein said separation device isolates the directly scattered light component from the at least one multiply scattered light component in response to the polarization state of the directly scattered light component relative to said series.

57. The imaging apparatus of claim 52, wherein said processor is adapted to populate a database with at least a portion of at least one said set of data.

58. The imaging apparatus of claim 57, wherein said database is adapted to distinguish an abnormal target from a normal target.

59. The imaging apparatus of claim 57, wherein said processor is adapted to couple said database to a training function.

60. The imaging apparatus of claim 52, wherein said processor is adapted to distinguish an abnormal target from a healthy target.

61. The imaging apparatus of claim 52, wherein said positioning element is adapted to vary the point of illumination in response to at least a portion of at least one said set of data.

* * * * *